(12) United States Patent
Kanjolia et al.

(10) Patent No.: US 8,481,121 B2
(45) Date of Patent: Jul. 9, 2013

(54) METHODS OF FORMING THIN METAL-CONTAINING FILMS BY CHEMICAL PHASE DEPOSITION

(75) Inventors: Ravi Kanjolia, North Andover, MA (US); Rajesh Odedra, Altrincham Cheshire (GB); Neil Boag, Mytholmroyd W. Yorkshire (GB); David Weyburne, Maynard, MA (US)

(73) Assignee: Sigma-Aldrich Co., LLC, St. Louis, MO (US)

( * ) Notice: Subject to any disclaimer, the term of this patent is extended or adjusted under 35 U.S.C. 154(b) by 409 days.

(21) Appl. No.: 12/670,023

(22) PCT Filed: Jul. 24, 2008

(86) PCT No.: PCT/US2008/071015
§ 371 (c)(1),
(2), (4) Date: May 10, 2010

(87) PCT Pub. No.: WO2009/015271
PCT Pub. Date: Jan. 29, 2009

(65) Prior Publication Data
US 2010/0261350 A1   Oct. 14, 2010

Related U.S. Application Data

(60) Provisional application No. 60/951,628, filed on Jul. 24, 2007.

(51) Int. Cl.
*C23C 16/06* (2006.01)
*C23C 16/16* (2006.01)

(52) U.S. Cl.
USPC ............. 427/255.28; 255/248.1; 255/124; 255/126.5

(58) Field of Classification Search
USPC ................ 427/248.1, 255.26, 255.28
See application file for complete search history.

(56) References Cited

U.S. PATENT DOCUMENTS

| 3,253,946 | A | * | 5/1966 | Kozikowski et al. | ......... 427/252 |
| 4,581,249 | A | | 4/1986 | Kamiya | ........ 427/53.1 |

(Continued)

FOREIGN PATENT DOCUMENTS

| JP | 2003-055390 | 2/2003 |
| JP | 2005-206925 | 8/2005 |

(Continued)

OTHER PUBLICATIONS

George, R., et al. (1995) "A comparison of the rates of alkyl migration in the complexes [CpM(CO)$_2$R] (M=Fe, Ru, Os; Cp = $\eta^5$-C$_5$H$_5$)"Journal of Organometallic Chemistry, 505:131-133.

(Continued)

*Primary Examiner* — David Turocy
(74) *Attorney, Agent, or Firm* — Harness, Dickey & Pierce, P.L.C.

(57) ABSTRACT

Methods of forming thin metal-containing films by chemical phase deposition, particularly atomic layer deposition (ALD) and chemical vapor deposition (CVD), are provided. The methods comprise delivering at least one organometallic precursor to a substrate, wherein the at least one precursor corresponds in structure to Formula (II); wherein: M is Ru, Fe or Os; R is Q-C$_{10}$-alkyl; X is C$_1$-C$_{10}$-alkyl; and n is zero, 1, 2, 3, 4 or 5. Further provided are methods of making precursors disclosed herein.

29 Claims, 14 Drawing Sheets

U.S. PATENT DOCUMENTS

| | | | |
|---|---|---|---|
| 6,420,583 B1* | 7/2002 | Lienhard et al. | 556/136 |
| 6,698,728 B1 | 3/2004 | Ravetz et al. | 261/121.1 |
| 7,282,119 B2 | 10/2007 | Odedra et al. | 203/29 |
| 7,419,698 B2 | 9/2008 | Jones | 427/248.1 |
| 8,039,062 B2 | 10/2011 | Heys et al. | 427/585 |
| 2005/0215805 A1 | 9/2005 | Meiere | 556/58 |
| 2006/0110930 A1* | 5/2006 | Senzaki | 438/758 |
| 2006/0121733 A1 | 6/2006 | Kilpela et al. | 438/681 |
| 2007/0190684 A1 | 8/2007 | Jones | 427/255.32 |
| 2008/0081127 A1* | 4/2008 | Thompson et al. | 427/569 |
| 2008/0248648 A1* | 10/2008 | Thompson et al. | 438/681 |
| 2008/0251016 A1 | 10/2008 | Cunning et al. | 118/722 |
| 2008/0282970 A1 | 11/2008 | Heys et al. | 117/104 |
| 2009/0043119 A1 | 2/2009 | Sekimoto et al. | 556/43 |
| 2009/0074983 A1 | 3/2009 | Heys et al. | 427/569 |
| 2010/0256406 A1 | 10/2010 | Kanjolia et al. | 556/136 |
| 2011/0021803 A1 | 1/2011 | Jin et al. | 558/150 |
| 2011/0151227 A1 | 6/2011 | Chalker et al. | 428/220 |
| 2011/0165401 A1 | 7/2011 | Chalker et al. | 428/220 |
| 2011/0165780 A1 | 7/2011 | Kanjolia et al. | 438/785 |
| 2011/0174416 A1 | 7/2011 | Hubsch et al. | 141/1 |
| 2011/0184156 A1 | 7/2011 | Jones | 534/15 |

FOREIGN PATENT DOCUMENTS

| | | |
|---|---|---|
| JP | 2005-146308 | 9/2005 |
| JP | 2006-128680 | 5/2006 |
| JP | 2007-084522 | 4/2007 |
| TW | 200540291 | 12/2005 |
| WO | WO 2006/131751 | 12/2006 |
| WO | WO 2007/057631 | 5/2007 |
| WO | WO 2009/015270 | 1/2009 |
| WO | WO 2009/015271 | 1/2009 |
| WO | WO 2009/036045 | 3/2009 |
| WO | WO 2009/036046 | 3/2009 |
| WO | WO 2009/086263 | 7/2009 |
| WO | WO 2009/117583 | 9/2009 |
| WO | WO 2009/143452 | 11/2009 |
| WO | WO 2009/143456 | 11/2009 |
| WO | WO 2009/143458 | 11/2009 |
| WO | WO 2009/143460 | 11/2009 |
| WO | WO 2009/146423 | 12/2009 |
| WO | WO 2009/155507 | 12/2009 |
| WO | WO 2009/155520 | 12/2009 |
| WO | WO 2011/011299 | 1/2011 |
| WO | WO 2011/017068 | 2/2011 |
| WO | WO 2011/053505 | 5/2011 |
| WO | WO 2011/097100 | 8/2011 |
| WO | WO 2011/112413 | 9/2011 |
| WO | WO 2011/115878 | 9/2011 |

OTHER PUBLICATIONS

Office Action, dated Dec. 13, 2011 issued in U.S. Appl. No. 12/670,022.

Casey CP, et al. (1981), "Metal formyl and hydroxymethyl metal compounds", *Journal of Molecular Catalysis*, 13(1) 43-59.

Eilbracht P, et al. (1977), "C-C-Einfachbindungsspaltung 1,1-Dialkyl substituierter Cyclopentadiene durch $Fe_2(CO)_9$ unter Ausbildung von pi-Cyclopentadienyl-sigma-Alkyl-Eisen-Komplexen", *Journal of Organometallic Chemistry*, 135(1): C23-C25 (Abstract).

Emeran A, et al. (1991), "The synthesis, characterization and properties of long-chain alkyl complexes of the type [$CpM(CO)_2R$] (Cp = eta5-$C_5H_5$; M = Fe, Ru; R= n-$C_6H_{13}$ to n-$C_{12}H_{25}$)", *Journal of Organometallic Chemistry*, 405(2) 237-246.

George SM, et al. (1996), "Surface chemistry for atomic layer deposition", *J. Phys. Chem.*, 100:13121-13131.

Hill RO, et al. (1999), "The synthesis, characterization and properties of alkyl complexes of the type Cp*$Fe(CO)_2$R; the X-ray crystal and molecular structure of Cp*$Fe(CO)_2$(n-$C_5H_{11}$) and molecular orbital and density functional calculations on the beta-hydride elimination of $CpFe(CO)_2(CH_2CH_3)$", *Journal of Organometallic Chemistry*, 587(1):28-37.

International Search Report and Written Opinion in PCT/US2008/071014, dated Apr. 12, 2008.

International Search Report and Written Opinion in PCT/US2008/071015, dated Jun. 11, 2008.

Johnston LJ, et al. (1988), "Oxidative addition reactions of compounds of the type (eta5-$C_5Me_5$)Os(CO)LR (L=CO, $PMe_2Ph$; R=alkyl). The role of oxidized intermediates in electrophilic cleavage reactions of osmium-carbon sigma-bonds", *Organometallics*, 7(12): 2469-2475.

Joseph MF, et al. (1984), "Oxidative cleavage reactions of compounds of the type CpRuLL'R (L,L' = CO, $PPh_3$; R = Me, $PhCH_2$)" *Organometallics*, 3(11):1749-1754.

Joseph MF, et al. (1982), "Preparation and electrochemical studies of the compounds $\eta^5$-$C_5H_5$RuCOLR (L = CO, $PPh_3$)", *Inorganica Chimica Acta*, 64(3):L121-L122.

Lin, et al. (1985), "A metal-metal bonded dinuclear ruthenium ketene complex", *Journal of the Chinese Chemical Society*, 32(3):295-299.

Luithardt W, et al. (1997), "Metal incorporation into diamond-like carbon films from single source metal organic precursors", *Solid State Ionics*, 101-103: 91-96.

Mohlala MS, et al. (2007), "Floating catalyst CVD synthesis of carbon nanotubes from $CpFe(CO)_{2X}$(X = Me, I): Poisoning effects of I", *Journal of Organometallic Chemistry*, 692(14): 2965-2970.

Moss J (1996), "Metal alkyl complexes as models for catalytic intermediates", *Mol. Catal. A: Chem.*, 107:169-174.

Ochiai M, et al. (2007), "Synthesis and structure of a hydrido(hydrosilylene)ruthenium complex and its reactions with nitriles", *Angewandte Chemie, International Edition*, 46(43):8192-8194.

Potter RJ, et. al. (2005), "Deposition of $HfO_2$, $Gd_2O_3$ and $PrO_x$ by Liquid Injection ALD Techniques", *Chem. Vap. Deposition*, 11(3):159-169.

Roger C, et al. (1989), "Rapid and convenient sonochemically-assisted alkyl-metal synthesis", *Journal of Organometallic Chemistry*, 365(3): 347-350.

Stasunik A, et al. (1984), "Einige Beispiele zur Reaktivität des Dicarbonyl (eta5-pentamethyl cyclopentadienyl)ruthenumions [$C_5Me_5(CO)_2Ru$]", *Journal of Organometallic Chemistry*, 270: C18-C22 (Abstract).

Trakarnpruk W, et al. (1994), "Reactions of [$Ru(C_5Me_5)Cl]_4$ with enones and enals: $Ru(C_5Me_5)$ as a 'carboxophile'," *Organometallics*, 13(6):2423-2429.

Office Action for Japanese Application No. 2010-518383 dated Jan. 16, 2013.

Nakazawa, H., et al. (2005), "Catalytic C —C bond cleavage and C —Si bond formation in the reaction of Rcn with $Et_3SiH$ promoted by an iron complex", *Chemical Communications*, 31: 4004-4006.

Nakazawa, H., et al. (2007), "Iron-Complex-Catalyzed C —C bond cleavage of organonitriles: catalytic metathesis reaction between H —Si and R —Cn bonds to afford R —H and Si —CN bonds", *Chemistry, Asian Journal*, 2: 882-888.

Office Action with English Translation dated Apr. 23, 2013 issued in Japanese Application No. 2010-518382.

\* cited by examiner

| Material | Vapour pressure equation |
|---|---|
| Ru(iPrCp)$_2$ | Log10P(mTorr) = -2200.4/T(Kelvin) + 8.3978 |
| Ru(Cp)$_2$ | Log10P(mTorr) = -3221.6/T(Kelvin) + 10.881 |
| Ru(tBuCp)$_2$ | Log10P(mTorr) = -3407.9.T(Kelvin) + 11.697 |
| Ru(iBuCp)$_2$ | Log10P(mTorr) = -3016.1/T(Kelvin) + 11.191 |
| Ru(CpEt)$_2$ | Log10P(mTorr) = -2794.1/T(Kelvin) + 10.451 |
| Ru(nPrCp)$_2$ | Log10P(mTorr) = -1940.1/T(Kelvin) + 7.6696 |
| Ru(MeCp)$_2$ | Log10P(mTorr) = -3711.1/T(Kelvin) + 12.97 |
| CpRuMe (CO)$_2$ | Log10P(mTorr) = -2301.1/T(Kelvin) + 9.3144 |
| DMRU | Log10P(mTorr) = -3778.2/T(Kelvin) + 12.429 |
| RuCp(CO)$_2$Et | Log10P(mTorr) = -1928.1/T(Kelvin) + 8.4314 |
| Ru(MeCp)(Me)(CO)$_2$ | Log10P(mTorr) = -2985.7/T(Kelvin) + 11.821 |

Fig. 13

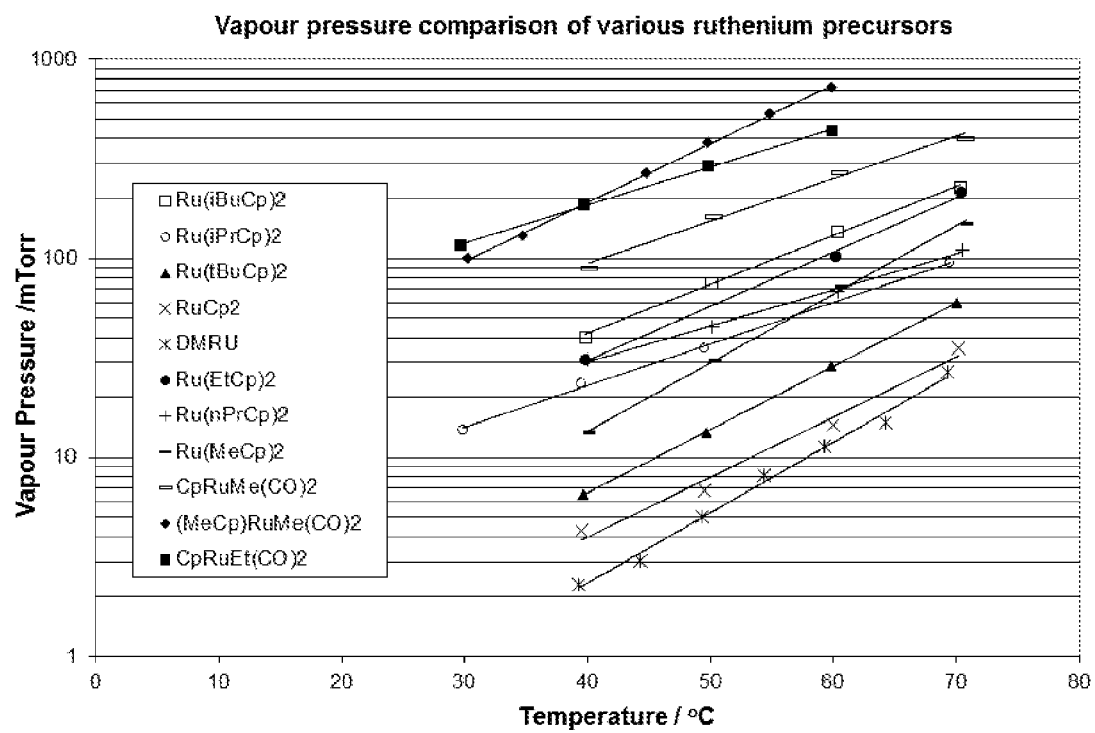

Fig. 14

|  |  |
|---|---|
| Yellow Crystalline Solid at 20°C | Yellow Liquid at 20°C |
| Boiling Point: 85°C @ 100 mtorr | Boiling Point: 60°C @ 100 mtorr |
| Thermally stable indefinitely at room temperature under $N_2$ | Thermally stable indefinitely at room temperature under $N_2$ |
Fig. 18

METHODS OF FORMING THIN METAL-CONTAINING FILMS BY CHEMICAL PHASE DEPOSITION

This patent claims priority to U.S. provisional patent application Ser. No. 60/951,628 filed on 24 Jul. 2007. This application contains subject matter that is related to U.S. provisional patent application Ser. No. 60/951,601, co-filed on 24 Jul. 2007. The disclosure of each of the applications identified in this paragraph is incorporated herein by reference in its entirety.

GOVERNMENT RIGHTS IN INVENTION

The United States government may have certain rights in this invention.

FIELD OF THE INVENTION

The present invention relates to methods of forming thin metal-containing films by chemical phase deposition processes, such as chemical vapor deposition (CVD) or atomic layer deposition (ALD).

BACKGROUND OF THE INVENTION

Various organometallic precursors are used to form high-K dielectric thin metal films for use in the semiconductor industry. Various deposition processes are used to form metal-containing films, such as chemical vapor deposition ("CVD") or atomic layer deposition ("ALD"), also known at atomic layer epitaxy. Organometallic precursors deposited by such chemical phase deposition processes have applications in nanotechnology and fabrication of semiconductor devices such as capacitor electrodes, gate electrodes, adhesive diffusion barriers and integrated circuits.

CVD is a chemical process whereby precursors are deposited on a substrate to form a solid thin film. In a typical CVD process, the precursors are passed over a substrate (wafer) within a low pressure or ambient pressure reaction chamber. The precursors react and/or decompose on the substrate surface creating a thin film of the desired material. Volatile byproducts are removed by gas flow through the reaction chamber. The deposition film thickness can be difficult to control because it depends on coordination of many parameters such as temperature, pressure, gas flow volumes and uniformity, chemical depletion effects and time.

ALD is a chemical process similar to CVD, except the ALD process separates the precursors during the reaction. The first precursor is passed over the substrate producing a monolayer on the substrate. Any excess unreacted precursor is pumped out of the reaction chamber. A second precursor is then passed over the substrate and reacts with the first precursor, forming a monolayer of film on the substrate surface. This cycle is repeated to create a film of desired thickness. ALD film growth is self-limited and based on surface reactions, creating uniform depositions that can be controlled at the nanometer scale.

Moss J., Mol. Catal. A: Chem., 107:169-174 (1996) reports an investigation and characterization of metal alkyl complexes of the type $RMn(CO)_5$ (R=alkyl group) and $CpM(CO)_2R$ ($Cp=\eta^5-C_5H_5$, M=Fe, Ru or Os), and binuclear complexes $Cp(CO)_2Ru(CH_2)_2Ru(CO)_2Cp$.

Current precursors for use in chemical phase deposition display low volatility, poor growth control and an inability to scale up. Therefore, there is a need for improved chemical phase deposition precursors, particularly for use in ALD and CVD, which display higher thermal stability, better adhesion, higher vapor pressure and carbon free layers.

SUMMARY OF THE INVENTION

There is now provided a method of forming a metal-containing thin film by ALD. The method comprises delivering at least one precursor to a substrate, wherein the precursor corresponds in structure to Formula II:

$$Cp(R)_nM(CO)_2(X) \qquad \text{(Formula II)}$$

wherein:
M is Ru, Fe or Os;
R is $C_1$-$C_{10}$-alkyl;
X is $C_1$-$C_{10}$-alkyl;
n is zero, 1, 2, 3, 4 or 5.

Further provided is a method of forming a metal-containing thin film by CVD. The method comprises delivering at least one precursor to a substrate, wherein the precursor corresponds in structure to Formula II above.

A method of preparing a ruthenium precursor of Formula I and/or II is also provided. The method comprises:
reacting $Ru_3(CO)_{12}$ with $3(CpR_n)H$ to yield $3Ru(CpR_n)(CO)_2H$ and $6CO$;
reacting $Ru(CpR_n)(CO)_2H$ with BuLi to yield $Li[Ru(CpR_n)(CO)_2]$ and BuH;
reacting $Li[Ru(CpR_n)(CO)_2]$ with XBr to yield $Ru(CpR_n)(CO)_2X$ and LiBr;
wherein:
X is $C_1$-$C_{10}$-alkyl;
R is $C_1$-$C_{10}$-alkyl;
and n is 0, 1, 2, 3, 4 or 5.

Other embodiments, including particular aspects of the embodiments summarized above, will be evident from the detailed description that follows.

BRIEF DESCRIPTION OF THE DRAWINGS

FIG. 13 is a vapor pressure equation table demonstrating a higher vapor pressure for CpRuMe(CO)$_2$ [(cyclopentadienyl) ruthenium(methyl)(dicarbonyl)], CpRu(Et)(CO)$_2$ [(cyclopentadienyl)ruthenium(ethyl)(dicarbonyl)], and (MeCp) Ru (Me)(CO)$_2$ [(methylcyclopentadienyl)ruthenium(methyl) (dicarbonyl)] versus other standard precursors.

FIG. 14 is a graphical representation demonstrating higher vapor pressures for the precursors of FIG. 13 compared to various standard precursors.

FIG. 18 is a table comparing physical data of CpRu(Me) (CO)$_2$ and CpRu(Et)(CO)$_2$.

DETAILED DESCRIPTION OF THE INVENTION

Figure 1:
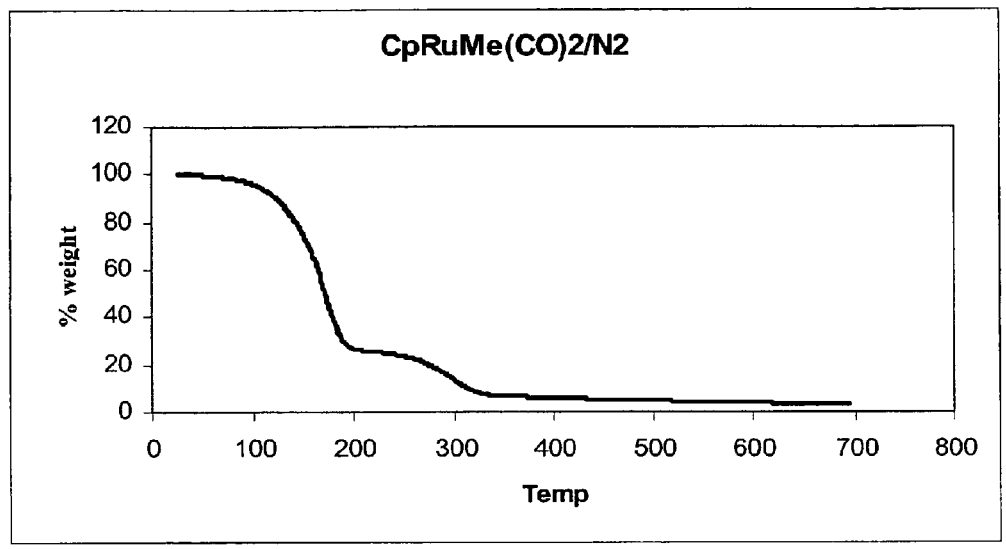
FIG. 1 is a graphical representation of thermogravimetric analysis (TGA) data demonstrating % weight vs. temperature of $CpRu(Me)(CO)_2$ [also referred to here in as (cyclopentadienyl)ruthenium(methyl)(dicarbonyl)] under $N_2$ conditions.
Figure 2:
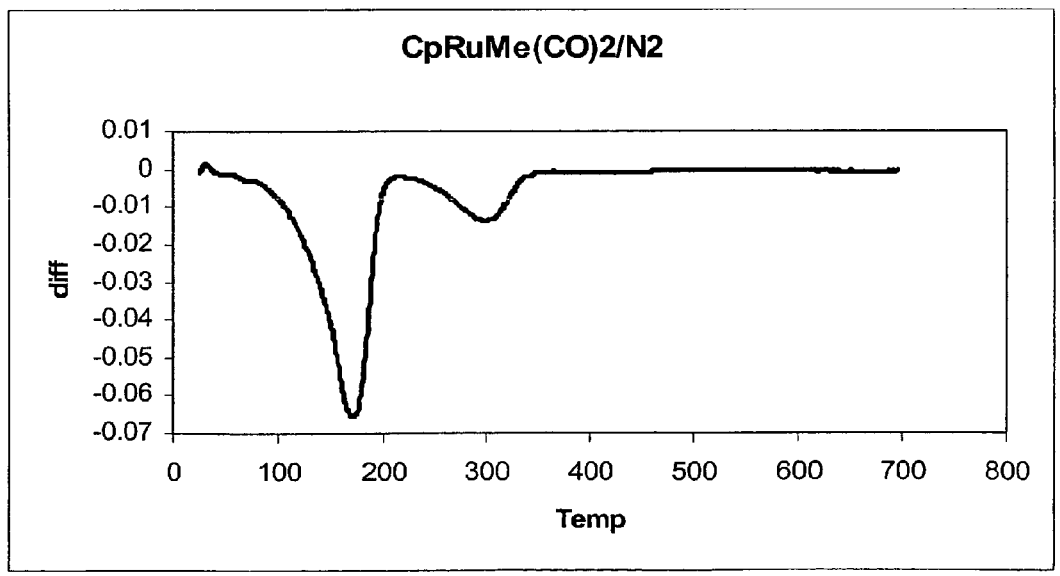
FIG. 2 is a graphical representation of TGA data demonstrating differential vs. temperature of $CpRu(Me)(CO)_2$ under $N_2$ conditions.
Figure 3:
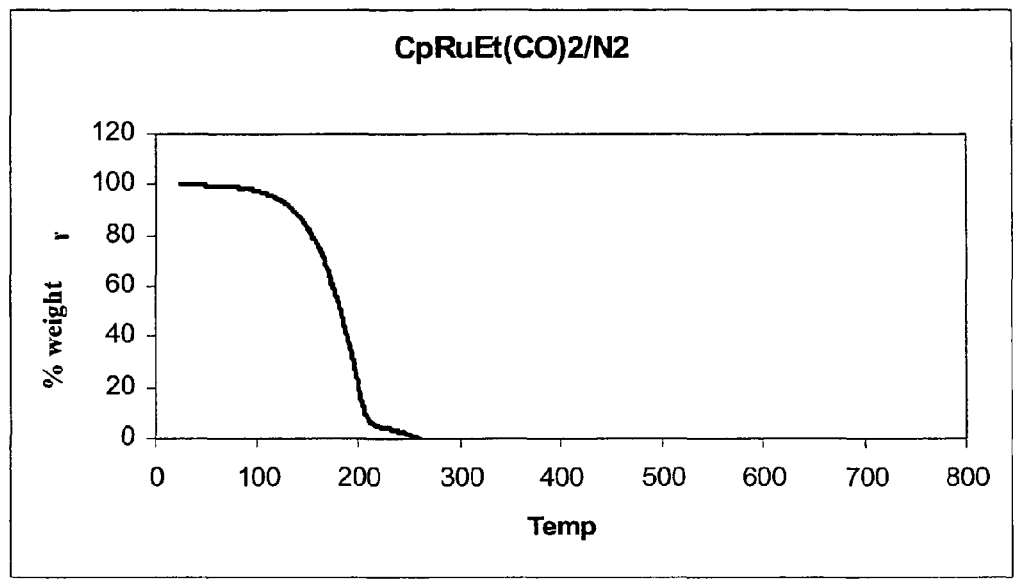
FIG. 3 is a graphical representation of TGA data demonstrating % weight vs. temperature of $CpRu(Et)(CO)_2$ [also referred to here in as (cyclopentadienyl)ruthenium(ethyl)(dicarbonyl)] under $N_2$ conditions.
Figure 4:
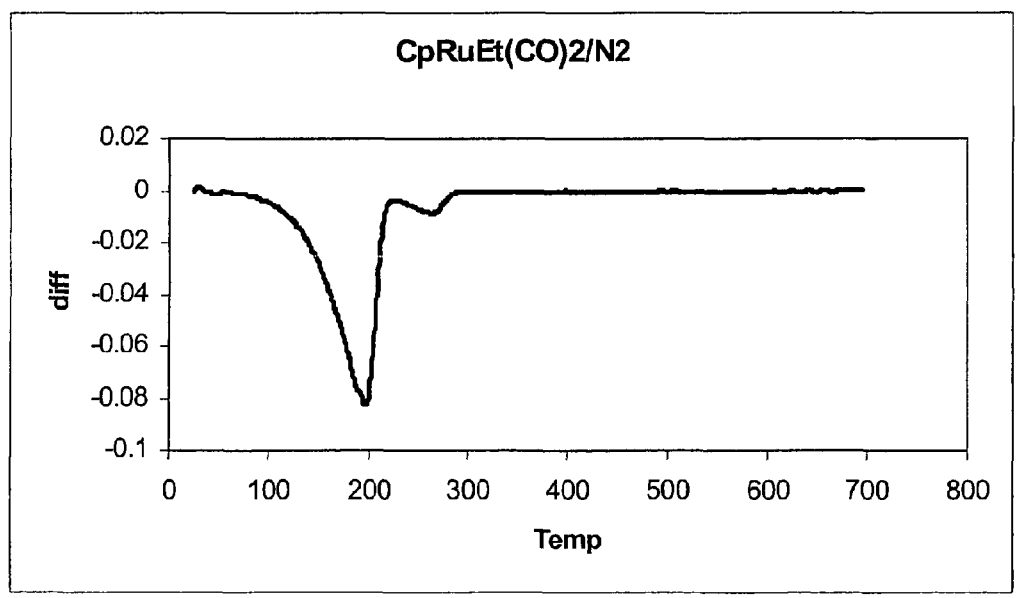
FIG. 4 is a graphical representation of TGA data demonstrating differential vs. temperature of $CpRu(Et)(CO)_2$ under $N_2$ conditions.
Figure 5:
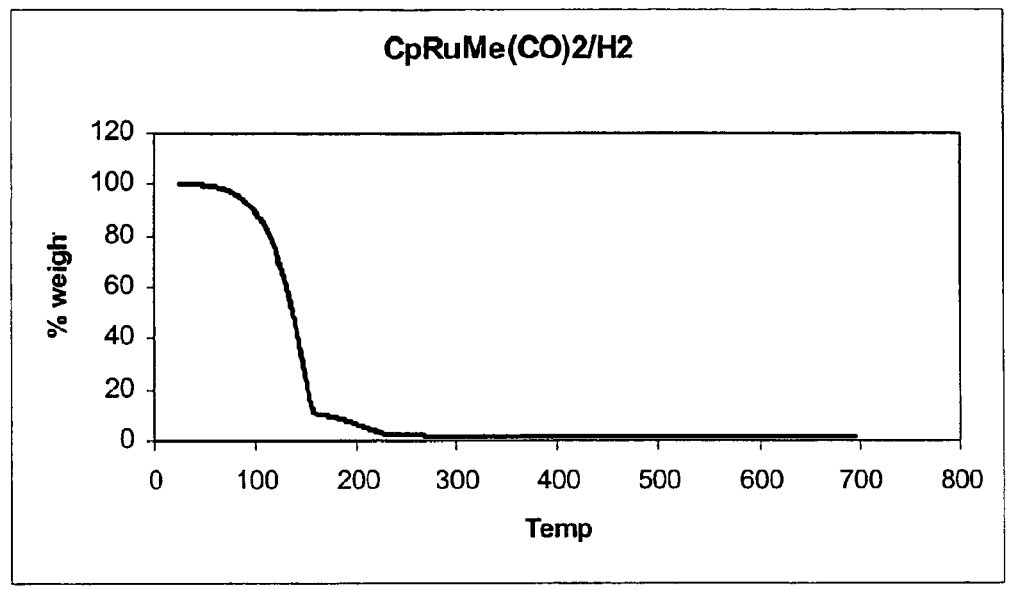
FIG. 5 is a graphical representation of TGA data demonstrating % weight vs. temperature of $CpRu(Me)(CO)_2$ under hydrogen conditions.
Figure 6:
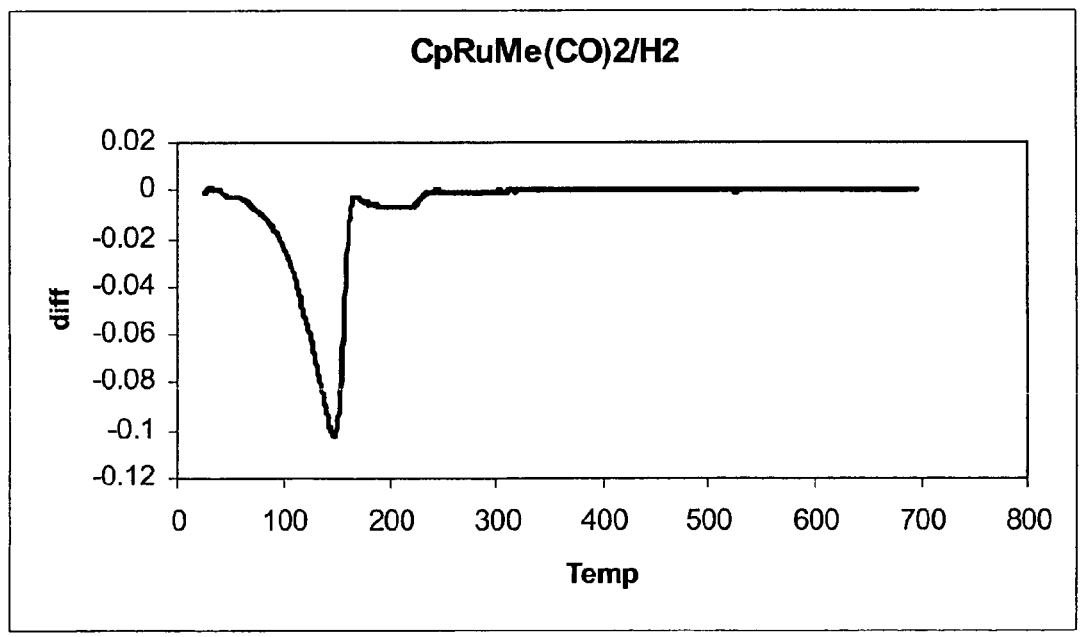
FIG. 6 is a graphical representation of TGA data demonstrating differential vs. temperature of $CpRu(Me)(CO)_2$ under hydrogen conditions.
Figure 7:
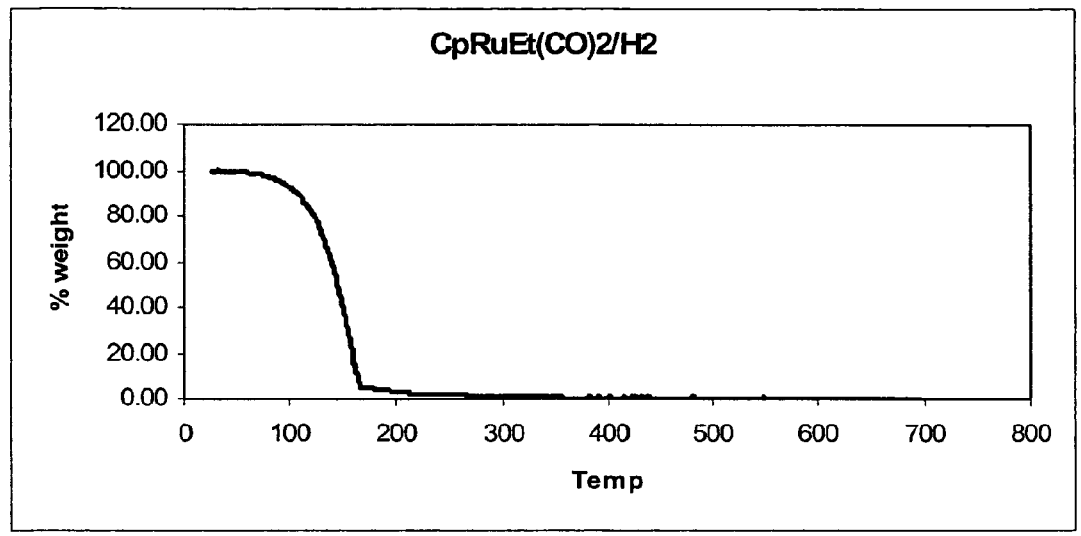
FIG. 7 is a graphical representation of TGA data demonstrating % weight vs. temperature of $CpRu(Et)(CO)_2$ under hydrogen conditions.
Figure 8:
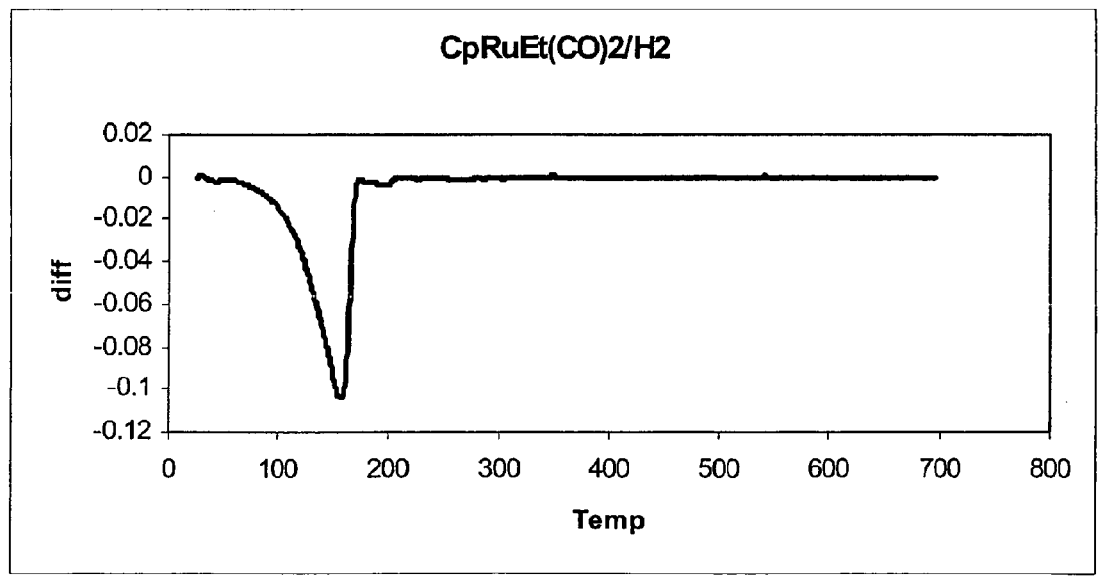
FIG. 8 is a graphical representation of TGA data demonstrating differential vs. temperature of $CpRu(Et)(CO)_2$ under hydrogen conditions.
Figure 9:
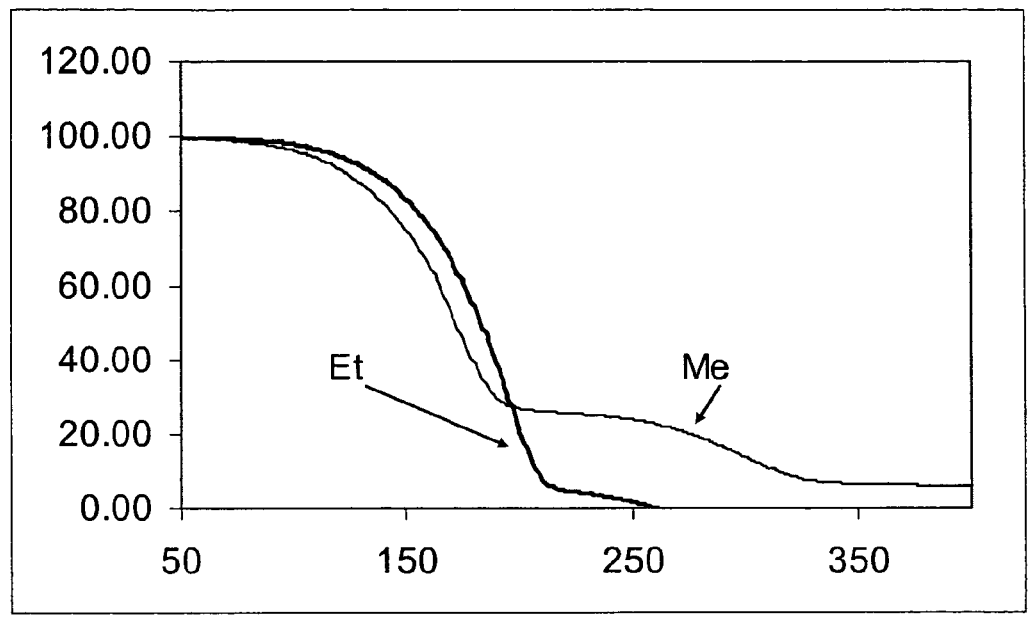
FIG. 9 is a graphical representation of TGA data comparing % weight (y axis) vs. temperature (x axis) of $CpRu(Me)(CO)_2$ and $CpRu(Et)(CO)_2$ under oxygen conditions.

In various aspects of the invention, methods are provided which are useful for forming thin metal-containing films, such as metal or metal oxide films, by chemical phase deposition processes, particularly CVD and ALD. Methods are also provided for making the organometallic precursors of Formula I and/or II.

The methods of the invention are used to create, grow or form thin metal-containing films which display high dielectric constants. A dielectric thin film as used herein refers to a thin film having a high permittivity.

As used herein, the term "precursor" refers to an organometallic molecule, complex and/or compound which is delivered to a substrate for deposition to form a thin film by a chemical deposition process, such as chemical vapor deposition or atomic layer deposition.

In a particular embodiment, the precursor may be dissolved in an appropriate hydrocarbon or amine solvent. Appropriate hydrocarbon solvents include, but are not limited to aliphatic hydrocarbons, such as hexane, heptane and nonane; aromatic hydrocarbons, such as toluene and xylene; aliphatic and cyclic ethers, such as diglyme, triglyme and tetraglyme. Examples of appropriate amine solvents include, without limitation, octylamine and N,N-dimethyldodecylamine. For example, the precursor may be dissolved in toluene to yield a 0.05 to 1M solution.

The term "Cp" refers to a cyclopentadienyl (C$_5$H$_5$) ligand which is bound to a transitional metal. As used herein, all five carbon atoms of the Cp ligand are bound to the metal center in $\eta^5$-coordination by $\pi$ bonding, therefore the precursors of the invention are $\pi$ complexes.

The term "alkyl" refers to a saturated hydrocarbon chain of 1 to 10 carbon atoms in length, such as, but not limited to, methyl, ethyl, propyl and butyl. The alkyl group may be straight-chain or branched-chain. For example, as used herein, propyl encompasses both n-propyl and iso-propyl; butyl encompasses n-butyl, sec-butyl, iso-butyl and tert-butyl. Further, as used herein, "Me" refers to methyl, and "Et" refers to ethyl.

The organometallic precursors of the invention have at least one metallic center comprising a transition metal ("M"). Examples of transition metals for use in the invention include, but are not limited to Sc, Y, La, Ti, Hf, Nb, Ta, Mn, Re, Fe, Ru, Os, Co, Rh, Ni, Pd, Pt, Cu, Ag and Au. In particular, there is one metal center and M is Ru, Os or Fe. In a further particular embodiment, M is Ru.

Therefore, in one embodiment an organometallic precursor is provided which corresponds in structure to Formula I:

$$Cp(R)_nM(CO)_2(X) \qquad \text{(Formula I)}$$

wherein:
M is Ru, Fe or Os;
R is $C_1$-$C_{10}$-alkyl;
X is $C_1$-$C_{10}$-alkyl; and
n is 1, 2, 3, 4 or 5.

In one aspect of the embodiment, the precursor corresponds in structure to Formula I wherein:
M is Ru;
R is selected from the group consisting of methyl, ethyl, propyl and butyl;
X is selected from the group consisting of methyl, ethyl, propyl and butyl; and
n is 1, 2, 3, 4 or 5.

In another aspect of the embodiment, the precursor corresponds in structure to Formula I wherein:
M is Os;
R is selected from the group consisting of methyl, ethyl, propyl and butyl;
X is selected from the group consisting of methyl, ethyl, propyl and butyl; and
n is 1, 2, 3, 4 or 5.

In another aspect of the embodiment, the precursor corresponds in structure to Formula I wherein:
M is Fe;
R is selected from the group consisting of methyl, ethyl, propyl and butyl;
X is selected from the group consisting of methyl, ethyl, propyl and butyl; and
n is 1, 2, 3, 4 or 5.

In another aspect of the embodiment, the precursor corresponds in structure to Formula I, wherein:
X is selected from the group consisting of methyl, ethyl and propyl;
R is selected from the group consisting of methyl, ethyl and propyl; and
n is 2, 3, 4, or 5.

In another aspect of the embodiment, the precursor corresponds in structure to Formula I, wherein:
M is Ru;
X is methyl or ethyl;
R is methyl or ethyl; and
n is 1.

In another aspect of the embodiment, the precursor corresponds in structure to Formula I, wherein:
M is Os;
X is methyl or ethyl;
R is methyl or ethyl; and
n is 1.

In another aspect of the embodiment, the precursor corresponds in structure to Formula I, wherein:
M is Fe;
X is methyl or ethyl;

R is methyl or ethyl; and
n is 1.

In particular, the precursor corresponding in structure to Formula I, is selected from the group consisting of:
(methylcyclopentadienyl)ruthenium(methyl)(dicarbonyl);
(ethylcyclopentadienyl)ruthenium(methyl)(dicarbonyl);
(propylcyclopentadienyl)ruthenium(methyl)(dicarbonyl);
(butylcyclopentadienyl)ruthenium(methyl)(dicarbonyl);
(methylcyclopentadienyl)ruthenium(ethyl)(dicarbonyl);
(ethylcyclopentadienyl)ruthenium(ethyl)(dicarbonyl);
(propylcyclopentadienyl)ruthenium(ethyl)(dicarbonyl);
(butylcyclopentadienyl)ruthenium(ethyl)(dicarbonyl);
(methylcyclopentadienyl)iron(methyl)(dicarbonyl);
(ethylcyclopentadienyl)iron(methyl)(dicarbonyl);
(propylcyclopentadienyl)iron(methyl)(dicarbonyl);
(butylcyclopentadienyl)iron(methyl)(dicarbonyl);
(methylcyclopentadienyl)iron(ethyl)(dicarbonyl);
(ethylcyclopentadienyl)iron(ethyl)(dicarbonyl);
(propylcyclopentadienyl)iron(ethyl)(dicarbonyl);
(butylcyclopentadienyl)iron(ethyl)(dicarbonyl);
(methylcyclopentadienyl)osmium(methyl)(dicarbonyl);
(ethylcyclopentadienyl)osmium(methyl)(dicarbonyl);
(propylcyclopentadienyl)osmium(methyl)(dicarbonyl);
(butylcyclopentadienyl)osmium(methyl)(dicarbonyl);
(methylcyclopentadienyl)osmium(ethyl)(dicarbonyl);
(ethylcyclopentadienyl)osmium(ethyl)(dicarbonyl);
(propylcyclopentadienyl)osmium(ethyl)(dicarbonyl); and
(butylcyclopentadienyl)osmium(ethyl)(dicarbonyl).

It has been discovered that substitution of the Cp ring and tailoring of the alkyl group bonded to the metal has shown useful properties for chemical phase deposition processes such as CVD or ALD, or a hybrid of CVD and ALD. Examples of such useful properties include higher vapor pressure (as demonstrated in FIG. 14) and greater thermal stability (as demonstrated in FIGS. 1-9). Further, is has been discovered that addition of the alkyl groups provides better adhesion to the substrate, and carbon free layers under ALD conditions. Though substituted-Cp precursors have shown useful properties, it is possible to use both the substituted and unsubstituted Cp precursors of the present invention in chemical phase deposition processes.

Therefore, in yet another embodiment, a method of forming a metal-containing thin film by ALD is provided. The method comprises delivering at least one precursor to a substrate, wherein the precursor corresponds in structure to Formula II:

$$Cp(R)_nM(CO)_2(X) \quad \text{(Formula II)}$$

wherein:
M is Ru, Fe or Os;
R is $C_1$-$C_{10}$-alkyl;
X is $C_1$-$C_{10}$-alkyl;
n is zero, 1, 2, 3, 4 or 5.

And in another embodiment, a method of forming a metal-containing thin film by CVD is provided. The method comprises delivering at least one precursor to a substrate, wherein the precursor corresponds in structure to Formula II above.

In a particular embodiment, the precursor corresponds in structure to Formula II wherein:
M is Ru;
R is methyl, ethyl, propyl or butyl;
X is methyl, ethyl, propyl or butyl; and
n is zero, 1 or 2.

In a particular embodiment, the precursor corresponds in structure to Formula II wherein:
M is Ru;
R is methyl or ethyl;
X is methyl or ethyl; and
n is zero or 1.

In a particular embodiment, the precursor corresponds in structure to Formula II wherein:
M is Fe;
R is methyl, ethyl, propyl or butyl;
X is methyl, ethyl, propyl or butyl; and
n is zero, 1 or 2.

In a particular embodiment, the precursor corresponds in structure to Formula II wherein:
M is Fe;
R is methyl or ethyl;
X is methyl or ethyl; and
n is zero or 1.

In a particular embodiment, the precursor corresponds in structure to Formula II wherein:
M is Os;
R is methyl, ethyl, propyl or butyl;
X is methyl, ethyl, propyl or butyl; and
n is zero, 1 or 2.

In a particular embodiment, the precursor corresponds in structure to Formula II wherein:
M is Os;
R is methyl or ethyl;
X is methyl or ethyl; and
n is zero or 1.

In a particular embodiment of the invention, the precursor according to Formula II is selected from the group consisting of:
(cyclopentadienyl)ruthenium(methyl)(dicarbonyl);
(cyclopentadienyl)ruthenium(ethyl)(dicarbonyl);
(cyclopentadienyl)iron(methyl)(dicarbonyl);
(cyclopentadienyl)iron(ethyl)(dicarbonyl);
(cyclopentadienyl)osmium(methyl)(dicarbonyl);
(cyclopentadienyl)osmium(ethyl)(dicarbonyl);
(methylcyclopentadienyl)ruthenium(methyl)(dicarbonyl);
(ethylcyclopentadienyl)ruthenium(methyl)(dicarbonyl);
(propylcyclopentadienyl)ruthenium(methyl)(dicarbonyl);
(butylcyclopentadienyl)ruthenium(methyl)(dicarbonyl);
(methylcyclopentadienyl)ruthenium(ethyl)(dicarbonyl);
(ethylcyclopentadienyl)ruthenium(ethyl)(dicarbonyl);
(propylcyclopentadienyl)ruthenium(ethyl)(dicarbonyl);
(butylcyclopentadienyl)ruthenium(ethyl)(dicarbonyl);
(methylcyclopentadienyl)iron(methyl)(dicarbonyl);
(ethylcyclopentadienyl)iron(methyl)(dicarbonyl);
(propylcyclopentadienyl)iron(methyl)(dicarbonyl);
(butylcyclopentadienyl)iron(methyl)(dicarbonyl);
(methylcyclopentadienyl)iron(ethyl)(dicarbonyl);
(ethylcyclopentadienyl)iron(ethyl)(dicarbonyl);
(propylcyclopentadienyl)iron(ethyl)(dicarbonyl);
(butylcyclopentadienyl)iron(ethyl)(dicarbonyl);
(methylcyclopentadienyl)osmium(methyl)(dicarbonyl);
(ethylcyclopentadienyl)osmium(methyl)(dicarbonyl);
(propylcyclopentadienyl)osmium(methyl)(dicarbonyl);
(butylcyclopentadienyl)osmium(methyl)(dicarbonyl);
(methylcyclopentadienyl)osmium(ethyl)(dicarbonyl);
(ethylcyclopentadienyl)osmium(ethyl)(dicarbonyl);
(propylcyclopentadienyl)osmium(ethyl)(dicarbonyl); and
(butylcyclopentadienyl)osmium(ethyl)(dicarbonyl).

In a further particular embodiment, the precursor according to Formula II is selected from the group consisting of:
(cyclopentadienyl)ruthenium(methyl)(dicarbonyl);
(cyclopentadienyl)ruthenium(ethyl)(dicarbonyl);
(cyclopentadienyl)iron(methyl)(dicarbonyl);
(cyclopentadienyl)iron(ethyl)(dicarbonyl);
(cyclopentadienyl)osmium(methyl)(dicarbonyl); and
(cyclopentadienyl)osmium(ethyl)(dicarbonyl).

In a further particular embodiment, the precursor corresponding in structure to Formula II is (cyclopentadienyl)ruthenium(ethyl)(dicarbonyl).

In another embodiment, the precursor corresponds in structure to Formula I and/or II, wherein butyl is selected from the group consisting of n-butyl, sec-butyl, iso-butyl and tent-butyl.

In another embodiment, the precursor corresponds in structure to Formula I and/or II, wherein propyl is selected from the group consisting of n-propyl and iso-propyl.

The chemical phase deposition processes of the invention, such as ALD and CVD, can be used to form various metal-containing thin films, such as metal or metal oxide films, on substrates using at least one of the organometallic precursors according to Formula II. The film can be formed by the organometallic precursor independently or in combination with a co-reactant (can be referred to as co-precursor). Examples of such co-reactants include, but are not limited to hydrogen, hydrogen plasma, oxygen, air, water, ammonia, hydrazine, allylhydrazine, borane, silane, ozone or any combination thereof.

In one embodiment, the at least one precursor is delivered to the substrate in pulses alternating with pulses of an oxygen source to create a metal oxide film. Examples of such oxygen sources include, without limitation, $H_2O$, $O_2$ or ozone.

A variety of substrates can be used in the methods of the present invention. For example, the precursors according to Formula I and/or II may be delivered for deposition on substrates such as, but not limited to, silicon, silicon oxide, silicon nitride, tantalum, tantalum nitride, or copper.

The ALD and CVD methods of the invention encompass various types of ALD and CVD processes such as, but not limited to, conventional processes, liquid injection processes and photo-assisted processes.

In one embodiment, conventional CVD is used to form a metal-containing thin film using at least one precursor according to Formula I and/or II. For conventional CVD processes, see for example Smith, Donald (1995). *Thin-Film Deposition: Principles and Practice*. McGraw-Hill.

In another embodiment, liquid injection CVD is used to form a metal-containing thin film using at least one precursor according to Formula I and/or II.

Examples of liquid injection CVD growth conditions include, but are not limited to:
 (1) Substrate temperature: 200-600° C. on Si(100)
 (2) Evaporator temperature: about 200° C.
 (3) Reactor pressure: about 5 mbar
 (4) Solvent: toluene, or any solvent mentioned above
 (5) Solution concentration: about 0.05 M
 (6) Injection rate: about 30 $cm^3$ $hr^{-1}$
 (7) Argon flow rate: about 200 $cm^3$ $min^{-1}$
 (8) Oxygen flow rate: about 100 $cm^3$ $min^{-1}$
 (9) Run time: 10 min In another embodiment, photo-assisted CVD is used to form a metal-containing thin film using at least one precursor according to Formula I and/or IL In a further embodiment, conventional ALD is used to form a metal-containing thin film using at least one precursor according to Formula I and/or II. For conventional and/or pulsed injection ALD process see for example, George S. M., et. al. *J. Phys. Chem.* 1996. 100:13121-13131.

In another embodiment, liquid injection ALD is used form a metal-containing thin film using at least one precursor according to Formula I and/or II, wherein at least one liquid precursor is delivered to the reaction chamber by direct liquid injection as opposed to vapor draw by a bubbler. For liquid injection ALD process see, for example, Potter R. J., et. al. *Chem. Yap. Deposition.* 2005. 11(3):159.

Examples of liquid injection ALD growth conditions include, but are not limited to:
 (1) Substrate temperature: 160-300° C. on Si(100)
 (2) Evaporator temperature: about 175° C.
 (3) Reactor pressure: about 5 mbar.
 (4) Solvent: toluene, or any solvent mentioned above
 (5) Solution concentration: about 0.05 M
 (6) Injection rate: about 2.5 µl $pulse^{-1}$ (4 pulses $cycle^{-1}$)
 (7) Inert gas flow rate: about 200 $cm^3$ $min^{-1}$
 (8) Pulse sequence (sec.) (precursor/purge/$H_2O$/purge): will vary according to chamber size. Number of cycles: will vary according to desired film thickness.

In another embodiment, photo-assisted ALD is used to form a metal-containing thin film using at least one precursor according to Formula I and/or II. For photo-assisted ALD processes see, for example, U.S. Pat. No. 4,581,249.

Thus, the organometallic precursors, according to Formula I or II, utilized in these methods may be liquid, solid, or gaseous.

Ruthenium precursors of Formula I and/or II can be made by the following method:

reacting $Ru_3(CO)_{12}$ with $3(CpR_n)H$ to yield $3Ru(CpR_n)(CO)_2H$ and $6CO$;

reacting $2Ru(Cp)R_n(CO)2H$ with [O] to yield $Ru_2(CpR_n)_2(CO)_4$ and $H_2$;

reacting $Ru_2(CpR_n)_2(CO)_4$ and $2NaK$ to yield $2K[Ru(CpR_n)(CO)_2]$; and reacting $K[Ru(CpR_n)(CO)_2]$ and $XBr$ to yield $Cp(R)_nRu(CO)_2(X)$;

wherein:
 X is $C_1$-$C_{10}$-alkyl;
 R is $C_1$-$C_{10}$-alkyl;
 and n is 0, 1, 2, 3, 4 or 5.

Alternatively, ruthenium precursors of Formula I and/or II can be made by the following method:

reacting $Ru_3(CO)_{12}$ with $3(CpR_n)H$ to yield $3Ru(CpR_n)(CO)_2H$ and $6CO$;

reacting $Ru(CpR_n)(CO)_2H$ with BuLi to yield $Li[Ru(CpR_n)(CO)_2]$ and BuH;

reacting $Li[Ru(CpR_n)(CO)_2]$ with $XBr$ to yield $Ru(CpR_n)(CO)_2X$ and LiBr;

wherein:
 X is $C_1$-$C_{10}$-alkyl;
 R is $C_1$-$C_{10}$-alkyl;
 and n is 0, 1, 2, 3, 4 or 5.

The precursors and methods disclosed herein are useful in semiconductor devices and are useful for computer memory and logic applications, such as dynamic random access memory (DRAM) and complementary metal oxide semiconductor (CMOS) circuitry. They are useful in many applications such as capacitor electrodes, gate electrodes and as adhesive diffusion barrier metal.

Precursors contemplated by the invention include, but are not limited to those listed below. It will be noted that when n is zero, there is no R substituent and the cyclopentadienyl ligand is therefore unsubstituted. Further, the R substituent is σ-bonded and its depiction below represents that the cyclopentadienyl ligand may be substituted zero to five times.

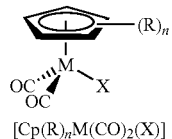

$[Cp(R)_nM(CO)_2(X)]$

| Precursor No. | M | X | R | n |
|---|---|---|---|---|
| 1 | Ru | CH$_3$ | — | 0 |
| 2 | Ru | CH$_3$ | CH$_3$ | 1 |
| 3 | Ru | CH$_3$ | CH$_3$ | 2 |
| 4 | Ru | CH$_3$ | CH$_3$ | 3 |
| 5 | Ru | CH$_3$ | CH$_3$ | 4 |
| 6 | Ru | CH$_3$ | CH$_3$ | 5 |
| 7 | Ru | CH$_3$ | — | 0 |
| 8 | Ru | CH$_3$ | C$_2$H$_5$ | 1 |
| 9 | Ru | CH$_3$ | C$_2$H$_5$ | 2 |
| 10 | Ru | CH$_3$ | C$_2$H$_5$ | 3 |
| 11 | Ru | CH$_3$ | C$_2$H$_5$ | 4 |
| 12 | Ru | CH$_3$ | C$_2$H$_5$ | 5 |
| 13 | Ru | CH$_3$ | — | 0 |
| 14 | Ru | CH$_3$ | propyl | 1 |
| 15 | Ru | CH$_3$ | propyl | 2 |
| 16 | Ru | CH$_3$ | propyl | 3 |
| 17 | Ru | CH$_3$ | propyl | 4 |
| 18 | Ru | CH$_3$ | propyl | 5 |
| 19 | Ru | CH$_3$ | — | 0 |
| 20 | Ru | CH$_3$ | butyl | 1 |
| 21 | Ru | CH$_3$ | butyl | 2 |
| 22 | Ru | CH$_3$ | butyl | 3 |
| 23 | Ru | CH$_3$ | butyl | 4 |
| 24 | Ru | CH$_3$ | butyl | 5 |
| 25 | Os | CH$_3$ | — | 0 |
| 26 | Os | CH$_3$ | CH$_3$ | 1 |
| 27 | Os | CH$_3$ | CH$_3$ | 2 |
| 28 | Os | CH$_3$ | CH$_3$ | 3 |
| 29 | Os | CH$_3$ | CH$_3$ | 4 |
| 30 | Os | CH$_3$ | CH$_3$ | 5 |
| 31 | Os | CH$_3$ | — | 0 |
| 32 | Os | CH$_3$ | C$_2$H$_5$ | 1 |
| 33 | Os | CH$_3$ | C$_2$H$_5$ | 2 |
| 34 | Os | CH$_3$ | C$_2$H$_5$ | 3 |
| 35 | Os | CH$_3$ | C$_2$H$_5$ | 4 |
| 36 | Os | CH$_3$ | C$_2$H$_5$ | 5 |
| 37 | Os | CH$_3$ | — | 0 |
| 38 | Os | CH$_3$ | propyl | 1 |
| 39 | Os | CH$_3$ | propyl | 2 |
| 40 | Os | CH$_3$ | propyl | 3 |
| 41 | Os | CH$_3$ | propyl | 4 |
| 42 | Os | CH$_3$ | propyl | 5 |
| 43 | Os | CH$_3$ | — | 0 |
| 44 | Os | CH$_3$ | butyl | 1 |
| 45 | Os | CH$_3$ | butyl | 2 |
| 46 | Os | CH$_3$ | butyl | 3 |
| 47 | Os | CH$_3$ | butyl | 4 |
| 48 | Os | CH$_3$ | butyl | 5 |
| 49 | Fe | CH$_3$ | — | 0 |
| 50 | Fe | CH$_3$ | CH$_3$ | 1 |
| 51 | Fe | CH$_3$ | CH$_3$ | 2 |
| 52 | Fe | CH$_3$ | CH$_3$ | 3 |
| 53 | Fe | CH$_3$ | CH$_3$ | 4 |
| 54 | Fe | CH$_3$ | CH$_3$ | 5 |
| 55 | Fe | CH$_3$ | — | 0 |
| 56 | Fe | CH$_3$ | C$_2$H$_5$ | 1 |
| 57 | Fe | CH$_3$ | C$_2$H$_5$ | 2 |
| 58 | Fe | CH$_3$ | C$_2$H$_5$ | 3 |
| 59 | Fe | CH$_3$ | C$_2$H$_5$ | 4 |
| 60 | Fe | CH$_3$ | C$_2$H$_5$ | 5 |
| 61 | Fe | CH$_3$ | — | 0 |
| 62 | Fe | CH$_3$ | propyl | 1 |
| 63 | Fe | CH$_3$ | propyl | 2 |
| 64 | Fe | CH$_3$ | propyl | 3 |
| 65 | Fe | CH$_3$ | propyl | 4 |
| 66 | Fe | CH$_3$ | propyl | 5 |
| 67 | Fe | CH$_3$ | — | 0 |
| 68 | Fe | CH$_3$ | butyl | 1 |
| 69 | Fe | CH$_3$ | butyl | 2 |

-continued

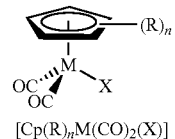

$[Cp(R)_nM(CO)_2(X)]$

| Precursor No. | M | X | R | n |
|---|---|---|---|---|
| 70 | Fe | CH$_3$ | butyl | 3 |
| 71 | Fe | CH$_3$ | butyl | 4 |
| 72 | Fe | CH$_3$ | butyl | 5 |
| 73 | Ru | C$_2$H$_5$ | — | 0 |
| 74 | Ru | C$_2$H$_5$ | CH$_3$ | 1 |
| 75 | Ru | C$_2$H$_5$ | CH$_3$ | 2 |
| 76 | Ru | C$_2$H$_5$ | CH$_3$ | 3 |
| 77 | Ru | C$_2$H$_5$ | CH$_3$ | 4 |
| 78 | Ru | C$_2$H$_5$ | CH$_3$ | 5 |
| 79 | Ru | C$_2$H$_5$ | — | 0 |
| 80 | Ru | C$_2$H$_5$ | C$_2$H$_5$ | 1 |
| 81 | Ru | C$_2$H$_5$ | C$_2$H$_5$ | 2 |
| 82 | Ru | C$_2$H$_5$ | C$_2$H$_5$ | 3 |
| 83 | Ru | C$_2$H$_5$ | C$_2$H$_5$ | 4 |
| 84 | Ru | C$_2$H$_5$ | C$_2$H$_5$ | 5 |
| 85 | Ru | C$_2$H$_5$ | — | 0 |
| 86 | Ru | C$_2$H$_5$ | propyl | 1 |
| 87 | Ru | C$_2$H$_5$ | propyl | 2 |
| 88 | Ru | C$_2$H$_5$ | propyl | 3 |
| 89 | Ru | C$_2$H$_5$ | propyl | 4 |
| 90 | Ru | C$_2$H$_5$ | propyl | 5 |
| 91 | Ru | C$_2$H$_5$ | — | 0 |
| 92 | Ru | C$_2$H$_5$ | butyl | 1 |
| 93 | Ru | C$_2$H$_5$ | butyl | 2 |
| 94 | Ru | C$_2$H$_5$ | butyl | 3 |
| 95 | Ru | C$_2$H$_5$ | butyl | 4 |
| 96 | Ru | C$_2$H$_5$ | butyl | 5 |
| 97 | Os | C$_2$H$_5$ | — | 0 |
| 98 | Os | C$_2$H$_5$ | CH$_3$ | 1 |
| 99 | Os | C$_2$H$_5$ | CH$_3$ | 2 |
| 100 | Os | C$_2$H$_5$ | CH$_3$ | 3 |
| 101 | Os | C$_2$H$_5$ | CH$_3$ | 4 |
| 102 | Os | C$_2$H$_5$ | CH$_3$ | 5 |
| 103 | Os | C$_2$H$_5$ | — | 0 |
| 104 | Os | C$_2$H$_5$ | C$_2$H$_5$ | 1 |
| 105 | Os | C$_2$H$_5$ | C$_2$H$_5$ | 2 |
| 106 | Os | C$_2$H$_5$ | C$_2$H$_5$ | 3 |
| 107 | Os | C$_2$H$_5$ | C$_2$H$_5$ | 4 |
| 108 | Os | C$_2$H$_5$ | C$_2$H$_5$ | 5 |
| 109 | Os | C$_2$H$_5$ | — | 0 |
| 110 | Os | C$_2$H$_5$ | propyl | 1 |
| 111 | Os | C$_2$H$_5$ | propyl | 2 |
| 112 | Os | C$_2$H$_5$ | propyl | 3 |
| 113 | Os | C$_2$H$_5$ | propyl | 4 |
| 114 | Os | C$_2$H$_5$ | propyl | 5 |
| 115 | Os | C$_2$H$_5$ | — | 0 |
| 116 | Os | C$_2$H$_5$ | butyl | 1 |
| 117 | Os | C$_2$H$_5$ | butyl | 2 |
| 118 | Os | C$_2$H$_5$ | butyl | 3 |
| 119 | Os | C$_2$H$_5$ | butyl | 4 |
| 120 | Os | C$_2$H$_5$ | butyl | 5 |
| 121 | Fe | C$_2$H$_5$ | — | 0 |
| 122 | Fe | C$_2$H$_5$ | CH$_3$ | 1 |
| 123 | Fe | C$_2$H$_5$ | CH$_3$ | 2 |
| 124 | Fe | C$_2$H$_5$ | CH$_3$ | 3 |
| 125 | Fe | C$_2$H$_5$ | CH$_3$ | 4 |
| 126 | Fe | C$_2$H$_5$ | CH$_3$ | 5 |
| 127 | Fe | C$_2$H$_5$ | — | 0 |
| 128 | Fe | C$_2$H$_5$ | C$_2$H$_5$ | 1 |
| 129 | Fe | C$_2$H$_5$ | C$_2$H$_5$ | 2 |
| 130 | Fe | C$_2$H$_5$ | C$_2$H$_5$ | 3 |
| 131 | Fe | C$_2$H$_5$ | C$_2$H$_5$ | 4 |
| 132 | Fe | C$_2$H$_5$ | C$_2$H$_5$ | 5 |
| 133 | Fe | C$_2$H$_5$ | — | 0 |
| 134 | Fe | C$_2$H$_5$ | propyl | 1 |
| 135 | Fe | C$_2$H$_5$ | propyl | 2 |
| 136 | Fe | C$_2$H$_5$ | propyl | 3 |
| 137 | Fe | C$_2$H$_5$ | propyl | 4 |
| 138 | Fe | C$_2$H$_5$ | propyl | 5 |

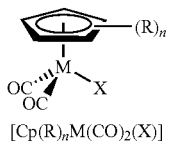

[Cp(R)$_n$M(CO)$_2$(X)]

| Precursor No. | M | X | R | n |
|---|---|---|---|---|
| 139 | Fe | C$_2$H$_5$ | — | 0 |
| 140 | Fe | C$_2$H$_5$ | butyl | 1 |
| 141 | Fe | C$_2$H$_5$ | butyl | 2 |
| 142 | Fe | C$_2$H$_5$ | butyl | 3 |
| 143 | Fe | C$_2$H$_5$ | butyl | 4 |
| 144 | Fe | C$_2$H$_5$ | butyl | 5 |
| 145 | Ru | propyl | — | 0 |
| 146 | Ru | propyl | CH$_3$ | 1 |
| 147 | Ru | propyl | CH$_3$ | 2 |
| 148 | Ru | propyl | CH$_3$ | 3 |
| 149 | Ru | propyl | CH$_3$ | 4 |
| 150 | Ru | propyl | CH$_3$ | 5 |
| 151 | Ru | propyl | — | 0 |
| 152 | Ru | propyl | C$_2$H$_5$ | 1 |
| 153 | Ru | propyl | C$_2$H$_5$ | 2 |
| 154 | Ru | propyl | C$_2$H$_5$ | 3 |
| 155 | Ru | propyl | C$_2$H$_5$ | 4 |
| 156 | Ru | propyl | C$_2$H$_5$ | 5 |
| 157 | Ru | propyl | — | 0 |
| 158 | Ru | propyl | isopropyl | 1 |
| 159 | Ru | propyl | isopropyl | 2 |
| 160 | Ru | propyl | isopropyl | 3 |
| 161 | Ru | propyl | isopropyl | 4 |
| 162 | Ru | propyl | isopropyl | 5 |
| 163 | Ru | propyl | — | 0 |
| 164 | Ru | propyl | tert-butyl | 1 |
| 165 | Ru | propyl | tert-butyl | 2 |
| 166 | Ru | propyl | tert-butyl | 3 |
| 167 | Ru | propyl | tert-butyl | 4 |
| 168 | Ru | propyl | tert-butyl | 5 |
| 169 | Os | propyl | — | 0 |
| 170 | Os | propyl | CH$_3$ | 1 |
| 171 | Os | propyl | CH$_3$ | 2 |
| 172 | Os | propyl | CH$_3$ | 3 |
| 173 | Os | propyl | CH$_3$ | 4 |
| 174 | Os | propyl | CH$_3$ | 5 |
| 175 | Os | propyl | — | 0 |
| 176 | Os | propyl | C$_2$H$_5$ | 1 |
| 177 | Os | propyl | C$_2$H$_5$ | 2 |
| 178 | Os | propyl | C$_2$H$_5$ | 3 |
| 179 | Os | propyl | C$_2$H$_5$ | 4 |
| 180 | Os | propyl | C$_2$H$_5$ | 5 |
| 181 | Os | propyl | — | 0 |
| 182 | Os | propyl | isopropyl | 1 |
| 183 | Os | propyl | isopropyl | 2 |
| 184 | Os | propyl | isopropyl | 3 |
| 185 | Os | propyl | isopropyl | 4 |
| 186 | Os | propyl | isopropyl | 5 |
| 187 | Os | propyl | — | 0 |
| 188 | Os | propyl | tert-butyl | 1 |
| 189 | Os | propyl | tert-butyl | 2 |
| 190 | Os | propyl | tert-butyl | 3 |
| 191 | Os | propyl | tert-butyl | 4 |
| 192 | Os | propyl | tert-butyl | 5 |
| 193 | Fe | propyl | — | 0 |
| 194 | Fe | propyl | CH$_3$ | 1 |
| 195 | Fe | propyl | CH$_3$ | 2 |
| 196 | Fe | propyl | CH$_3$ | 3 |
| 197 | Fe | propyl | CH$_3$ | 4 |
| 198 | Fe | propyl | CH$_3$ | 5 |
| 199 | Fe | propyl | — | 0 |
| 200 | Fe | propyl | C$_2$H$_5$ | 1 |
| 201 | Fe | propyl | C$_2$H$_5$ | 2 |
| 202 | Fe | propyl | C$_2$H$_5$ | 3 |
| 203 | Fe | propyl | C$_2$H$_5$ | 4 |
| 204 | Fe | propyl | C$_2$H$_5$ | 5 |
| 205 | Fe | propyl | — | 0 |
| 206 | Fe | propyl | isopropyl | 1 |
| 207 | Fe | propyl | isopropyl | 2 |

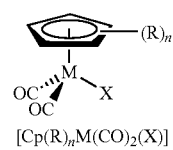

[Cp(R)$_n$M(CO)$_2$(X)]

| Precursor No. | M | X | R | n |
|---|---|---|---|---|
| 208 | Fe | propyl | isopropyl | 3 |
| 209 | Fe | propyl | isopropyl | 4 |
| 210 | Fe | propyl | isopropyl | 5 |
| 211 | Fe | propyl | — | 0 |
| 212 | Fe | propyl | tert-butyl | 1 |
| 213 | Fe | propyl | tert-butyl | 2 |
| 214 | Fe | propyl | tert-butyl | 3 |
| 215 | Fe | propyl | tert-butyl | 4 |
| 216 | Fe | propyl | tert-butyl | 5 |

EXAMPLES

The following examples are merely illustrative, and do not limit this disclosure in any way.

Example 1

The synthesis of Ru($\eta^5$-CpMe)(CO)$_2$Me [also referred to herein as (methylcyclopentadienyl)ruthenium(methyl)(dicarbonyl)] is demonstrated by the following two-step process.

Ru$_3$(CO)$_{12}$ (15.0 g, 23.5 mmols) was reacted with CpMeH in the normal manner except that solution was heated for 1.5 hours instead of 1.0 hour and reaction with oxygenated heptane for 2.5 hours rather than 2.0 hours. After cooling overnight, orange crystalline material (12.1 g, 73%) was obtained. The solution is reduced to 100 ml and a further (1.9 g, 11%) darker, crystalline material was obtained after standing overnight. Total yield 84%.

IR (hexane) 2007 m, 1968 m, 1960 s, 1940 m, 1788 s cm$^{-1}$; (CH$_2$Cl$_2$) 1997 s, 1953 s, 1767 s cm$^{-1}$.

NMR (C$_6$D$_6$) $^1$H $\delta$4.75 (m, 4H, CH), 4.54 (m, 4H, CH), 1.70 (s, 6H, CH$_3$); $^{13}$C{$^1$H} $\delta$ 221.7 (CO), 109.2 (C), 89.4 (CMe), 88.5 (CMe), 12.6 (Me).

Next, Ru$_2$($\eta^5$-CpMe)$_2$(CO)$_4$ (20.4 g, 43.2 mmols) was dissolved in degassed THF (~250 ml), the solution degassed again and NaK (7 ml) was added. Solution was stirred for 5-6 hours until sample quenched in MeI showed a complete reaction (2018, 1959 cm$^{-1}$). Unlike Ru$_2$($\eta^5$-Cp)$_2$(CO)$_4$ reaction, the quenched solution was pale yellow and the reduced solution was quite dark. There was no obvious precipitate. Solution makes up to ~700 ml. Solution filtered into MeI (20 ml) with occasional shaking. Solvent was removed on rotavap (~70 mm Hg) to give an oil which was dissolved in hexane (~150 ml). Following filtration, solvent was removed on the rotavap, the oil was transferred to a small flask and the residual hexane was removed at 0.5 mm Hg to give 22 g of a dark red oil. Distillation was performed twice at 58-60° C. (0.5 mm Hg) to give a pale yellow mobile oil (17.1 g, 79) of ($\eta^5$-CpMe)Ru(Me)(CO)$_2$ depicted below.

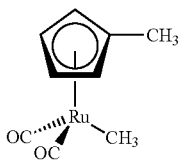

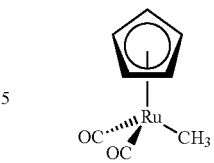

Example 2

A synthesis scheme to prepare CpRu(Et)(CO)$_2$ [also referred to herein as (cyclopentadienyl)ruthenium(ethyl)(dicarbonyl) and depicted below] is demonstrated below.

Ru$_3$(CO)$_{12}$+3CpH→3Ru(Cp)(CO)$_2$H+6CO

2Ru(Cp)(CO)$_2$H+[O]→Ru$_2$(Cp)$_2$(CO)$_4$+H$_2$

Ru$_2$(Cp)$_2$(CO)$_4$+2NaK→2K[Ru(Cp)(CO)$_2$]

K[Ru(Cp)(CO)$_2$]+EtBr→Ru(Cp)(CO)$_2$Et+KBr

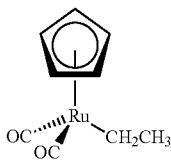

Example 3

A further synthesis scheme and a method to prepare CpRu(Et)(CO)$_2$ is demonstrated below.

Ru$_3$(CO)$_{12}$+3CpH→3Ru(Cp)(CO)$_2$H+6CO

Ru(Cp)(CO)$_2$H+BuLi→Li[Ru(Cp)(CO)$_2$]+BuH

Li[Ru(Cp)(CO)$_2$]+EtBr→Ru(Cp)(CO)$_2$Et+LiBr

All handling was under inert conditions. A suspension of Ru$_3$(CO)$_{12}$ (10.0 g, 15.6 mmol) in dry, degassed heptane (400 ml) and cracked cyclopentadiene (20.5 g, 310 mmol) was refluxed for 1 hour. The volume was reduced to 60 ml by distilling the solvent and unreacted cyclopentadiene in a stream of nitrogen and cooled. Dry degassed pentane (100 ml) was added followed by the dropwise addition of a hexane solution of 1.6 M BuLi in hexane (31 ml, 50 mmol). The solution was stirred for 1 hour and dry, degassed ethyl bromide (10.9 g 100 mmol) added dropwise. The mixture was stirred for a further 2 hours, filtered and the solvent removed in vacuo. The product was distilled up a short Vigreux column at 56° at 0.2 mmHg (9.4 g, 80%).

$^1$H-NMR (400 MHz, CDCl$_3$) ppm 5.23 (s, 5H, Cp), 1.77 (q, 2H, J=7.5 Hz, CH$_2$) ppm 1.37 (t, 1H, J=7.5 Hz, CH$_3$)

$^{13}$C{$^1$H} NMR 202.4 (CO), 88.6 (Cp), 24.2 (CH$_2$), 10.0 (CH$_3$)

ν(CO) (hexane) 2020, 1960 cm$^{-1}$

Example 4

ALD growth using CpRuMe(CO)$_2$ [also referred to herein as (cyclopentadienyl)ruthenium(methyl)(dicarbonyl)] and depicted below is demonstrated by the following example.

Ruthenium thin films were deposited in a custom-built ALD reactor. Cyclopentadienyl ruthenium(methyl)dicarbonyl (CpRuMe(CO)$_2$) and air were used as precursors. The ruthenium films were deposited on silicon wafer substrates. Prior to deposition, the wafer substrates were dipped in a 10% HF:water mixture for 30 seconds. The growth temperature was 300° C. The growth pressure is 250 milliTorr. The reactor is continuously purged with 30 scan of dry nitrogen. All the computer controlled valves in the reactor were the air operated ALD VCR valves from Cajon.

The amount of injected air was the volume trapped between the VCR gasket (a blank gasket with a 30 micron pin hole in it) and the ALD valve stem. For air at atmospheric pressure and temperature, this means that approximately 29 μmoles of air is pulsed into the reactor during the air injection cycle. The pulse length of the air precursor is approximately 1 second followed by a 2-5 second purge. No ruthenium was deposited when the air inject line was plugged.

The ruthenium was stored in a stainless steel ampoule. Attached directly to the ampoule was an air operated ALD valve. The output of this ALD valve was Tee'd with another ALD valve used for nitrogen injection. The Tee outlet leg was connected to a 500 cm$^3$ stainless steel reservoir. The outlet of the reservoir was attached to a third ALD valve, called the inject valve, whose outlet goes directly to the reactor. Nitrogen injection was used to build up the total pressure behind the ruthenium inject valve so that the pressure was higher than the reactor growth pressure. The injected nitrogen was accomplished using a 30 micron pin hole VCR gasket as described above for air injection. All of the valves and ampoule were placed into an oven-like enclosure that allowed the ampoule, valves, and tubing to be heated uniformly to 50° C. to 120° C.

During the ALD growth operation, the valves were sequenced in the following manner. Immediately after an air injection, the ruthenium ampoule ALD valve and the nitrogen inject ALD valve were both opened. The nitrogen inject valve was closed after 0.2 seconds. The ruthenium vapors and injected nitrogen were allowed to equilibrate in the 500 cm$^3$ reservoir during the air purge time (typically 2-5 seconds). After the air purge time had elapsed, the ruthenium ampoule ALD valve was closed, and after a 0.2 second wait time, the ruthenium inject valve was opened for 0.2 seconds. The ruthenium was allowed to purge from the reactor for typically 5 seconds. The air was then injected to start the ALD cycle all over again.

The effect of the dose of ruthenium precursor was investigated by varying the precursor temperature from 85° C. to 110° C. The growth at 85° C. is non-uniform. The growth with precursor temperature between 90° C. to 110° C. is uniform. Normal growth temperature is usually 90° C.

The total amount of cycles was 300. Results show that the deposition rate was independent of the ruthenium dose as varied through its vapor pressure, which in turn is varied through its evaporation temperature. This proves that the film growth proceeds in a self-limiting manner as is characteristic of ALD.

Figure 10:
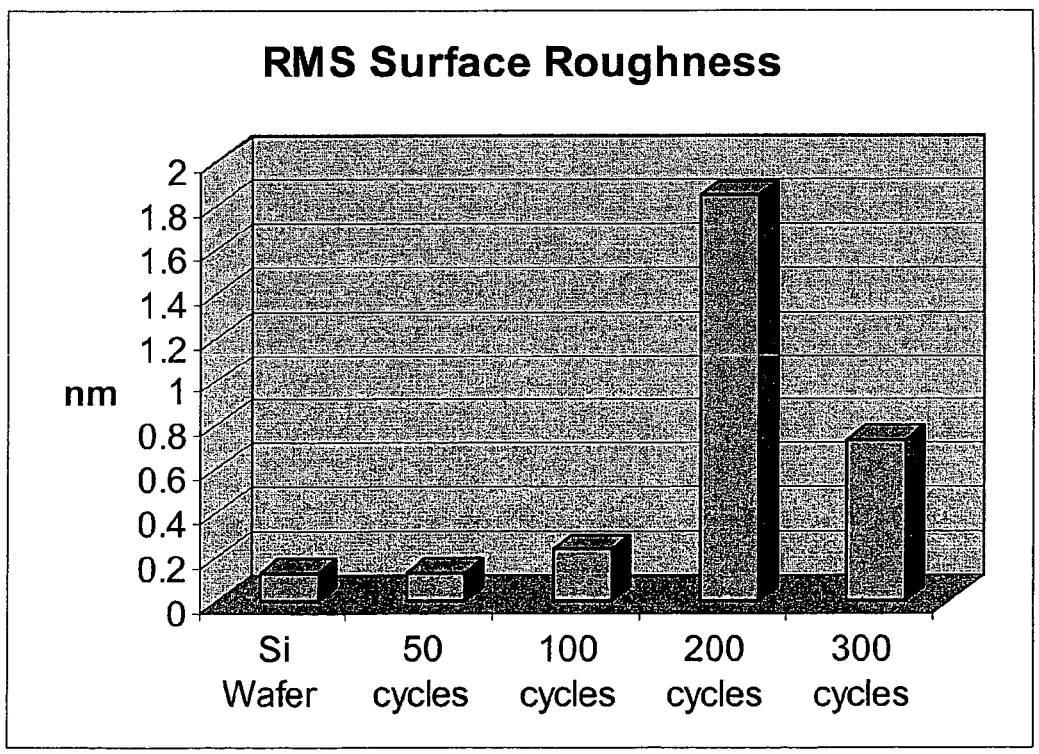
FIG. 10 is a graphical representation of root mean square ("RMS") surface roughness results obtained in Example 4.
Figure 11:
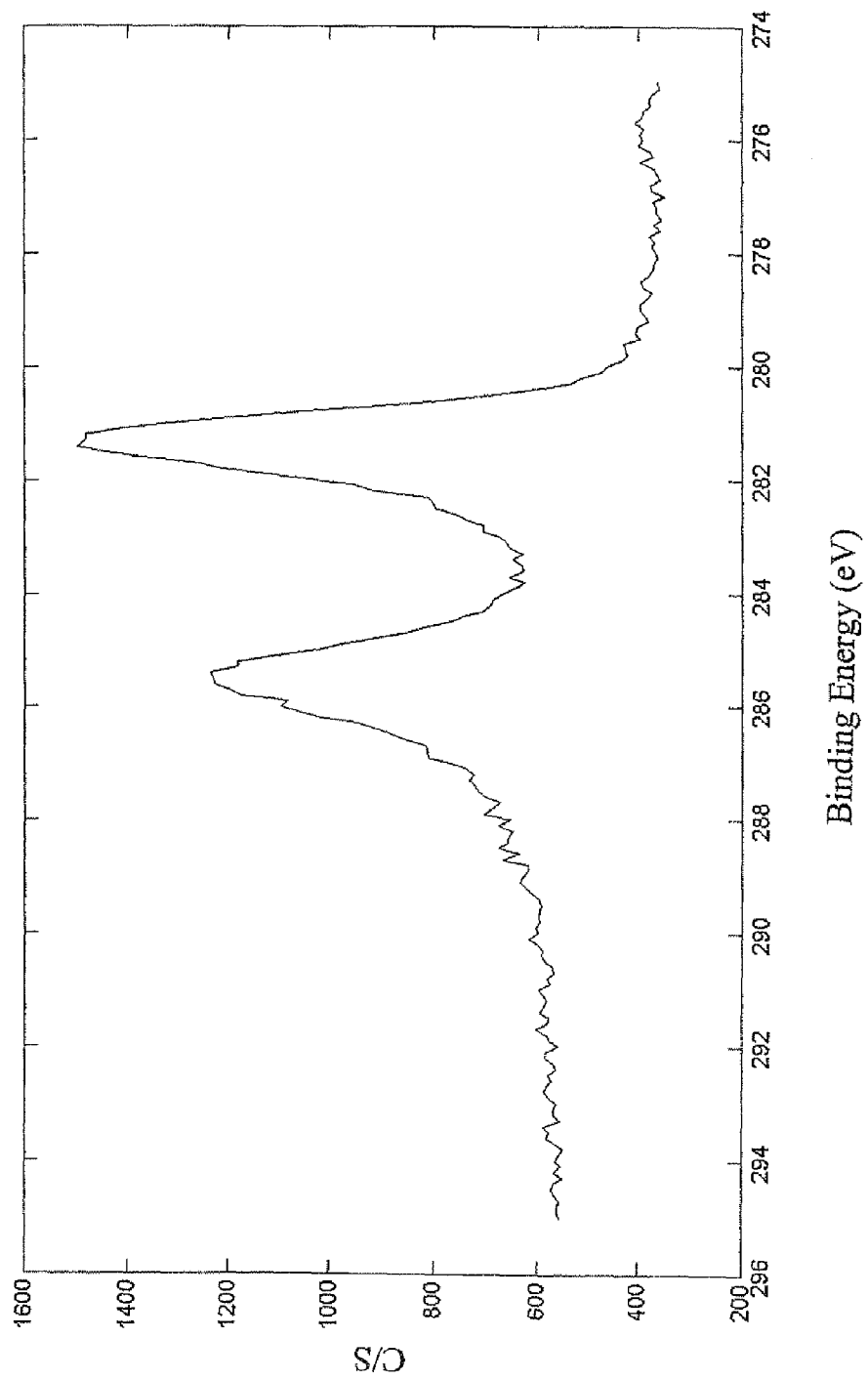
FIG. 11 is a graphical representation of X-ray photoelectron spectroscopy (XPS) data obtained from ALD (300 cycles) of CpRu(Me)(CO)$_2$ onto a tantalum nitride wafer with air as a co-precursor.
Figure 12:
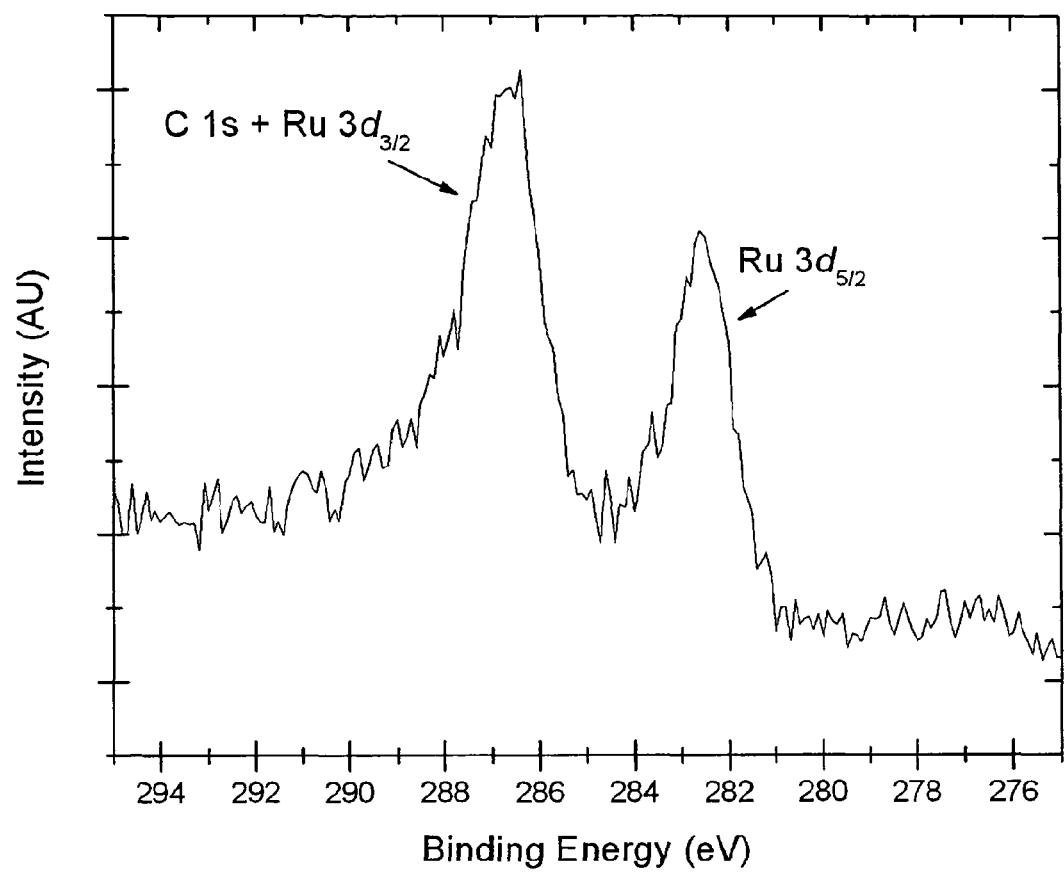
FIG. 12 is a graphical representation of XPS data obtained from ALD (300 cycles) of CpRu(Me)(CO)$_2$ onto a tantalum nitride wafer without air.
Figure 15:
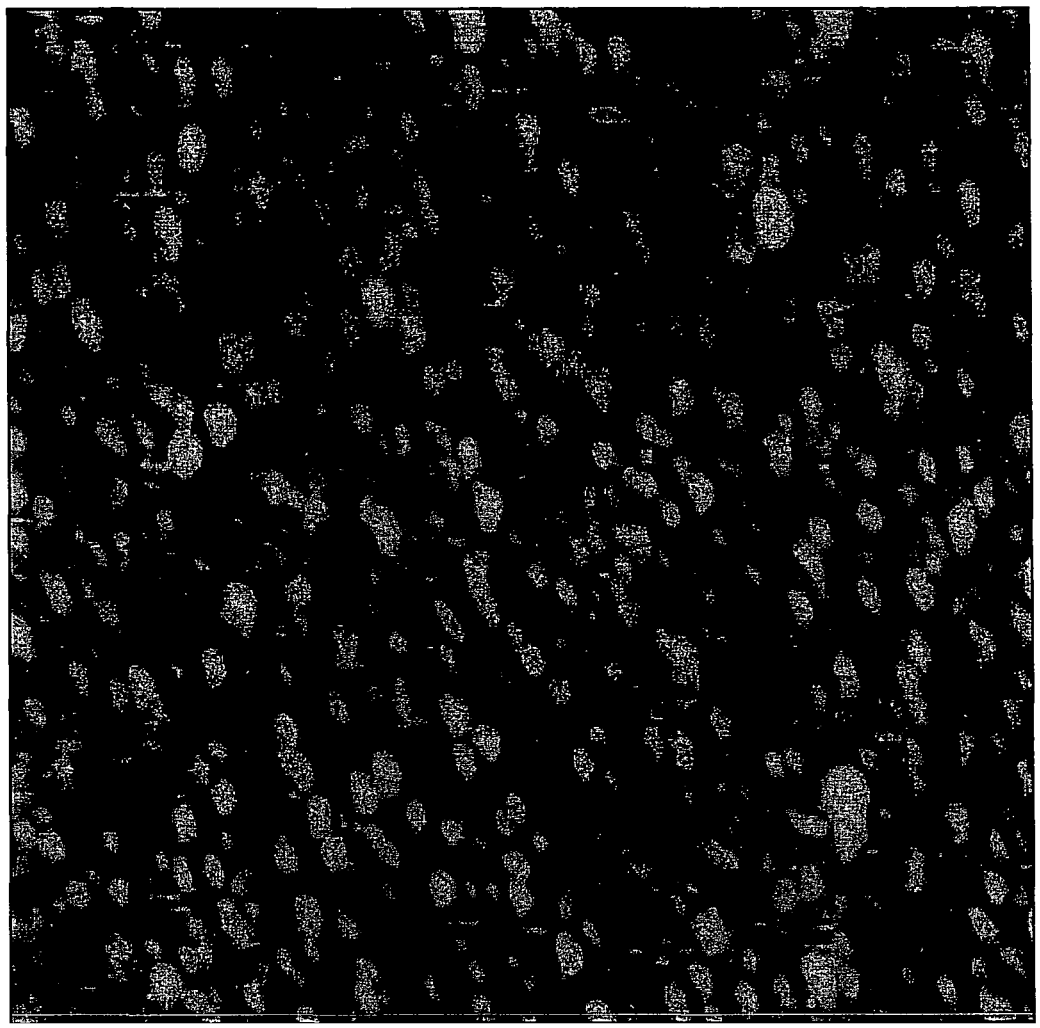
FIG. 15 is a scanning electron micrograph of a ruthenium film grown using ALD of CpRu(Me)(CO)$_2$, 300 cycles.

The films produce a featureless scanning electron micrograph as shown in FIG. 15. The resistivity of the films is 22-25 micro ohm cm. AFM spectroscopy at various cycles (50-300 cycles) shows the growth process via island formation. See FIG. 10. XPS of the ALD grown ruthenium films demonstrate the absence of carbon in the films. See FIGS. 11 and 12.

Example 5

ALD growth using $CpRuMe(CO)_2$ was also performed as in Example 4, except using an argon purge, as opposed to nitrogen, a ruthenium pulse length of 1 second, an air pulse length of 1 second.

Example 6

ALD growth using $CpRuEt(CO)_2$ [also referred to herein as (cyclopentadienyl)ruthenium(ethyl)(dicarbonyl)] and depicted below is demonstrated by the following example.

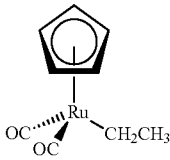

Ruthenium thin films were deposited in a custom-built ALD reactor. Cyclopentadienyl ruthenium (ethyl)dicarbonyl ($CpRuEt(CO)_2$) and air was used as precursors. The ruthenium films were deposited on silicon wafer substrates. Prior to deposition, the wafer substrates were dipped in a 10% HF:water mixture for 30 seconds. The growth temperature was 265° C. The growth pressure was 100 milliTorr. The reactor was continuously purged with 10 seem of argon. All the computer controlled valves in the reactor are the air operated ALD VCR valves from Cajon.

The amount of injected air was the volume trapped between the VCR gasket (a blank gasket with a 30 micron pin hole in it) and the ALD valve stem. For air at atmospheric pressure and temperature, this means that approximately 29 μmoles of air is pulsed into the reactor during the air injection cycle. The pulse length of the air precursor is approximately 2 seconds followed by a 2-5 second purge. No ruthenium was deposited when the air inject line was plugged.

The ruthenium was stored in a stainless steel ampoule. Attached directly to the ampoule was an air operated ALD valve. The output of this ALD valve was Tee'd with another ALD valve used for argon injection. The Tee outlet leg was connected to a 500 cm³ stainless steel reservoir. The outlet of the reservoir was attached to a third ALD valve, called the inject valve, whose outlet goes directly to the reactor. Argon injection was used to build up the total pressure behind the ruthenium inject valve so that the pressure is higher than the reactor growth pressure. The injected argon was accomplished using a 30 micron pin hole VCR gasket as described above for air injection. All of the valves and ampoule were placed into an oven-like enclosure that allowed the ampoule, valves, and tubing to be heated uniformly to 50° C. to 120° C.

During the ALD growth operation, the valves were sequenced in the following manner. Immediately after an air injection, the ruthenium ampoule ALD valve and the argon inject ALD valve were both opened. The argon inject valve was closed after 0.2 seconds. The ruthenium vapors and injected argon were allowed to equilibrate in the 500 cm³ reservoir during the air purge time (typically 2-5 seconds). After the air purge time had elapsed, the ruthenium ampoule ALD valve was closed, and after a 0.2 second wait time, the ruthenium inject valve was opened for 2 seconds. The ruthenium was allowed to purge from the reactor for typically 5 seconds. The air was then injected to start the ALD cycle all over again.

The effect of the dose of ruthenium precursor was investigated by varying the precursor temperature from 85° C. to 110° C. The growth at 85° C. is non-uniform. The growth with precursor temperature between 90° C. to 110° C. is uniform. Normal growth temperature is usually 90° C.

The total amount of cycles was 300. Results show that the deposition rate is independent of the ruthenium dose as varied through its vapor pressure, which in turn is varied through its evaporation temperature. This proves that the film growth proceeds in a self-limiting manner as is characteristic of ALD.

Figure 16A:
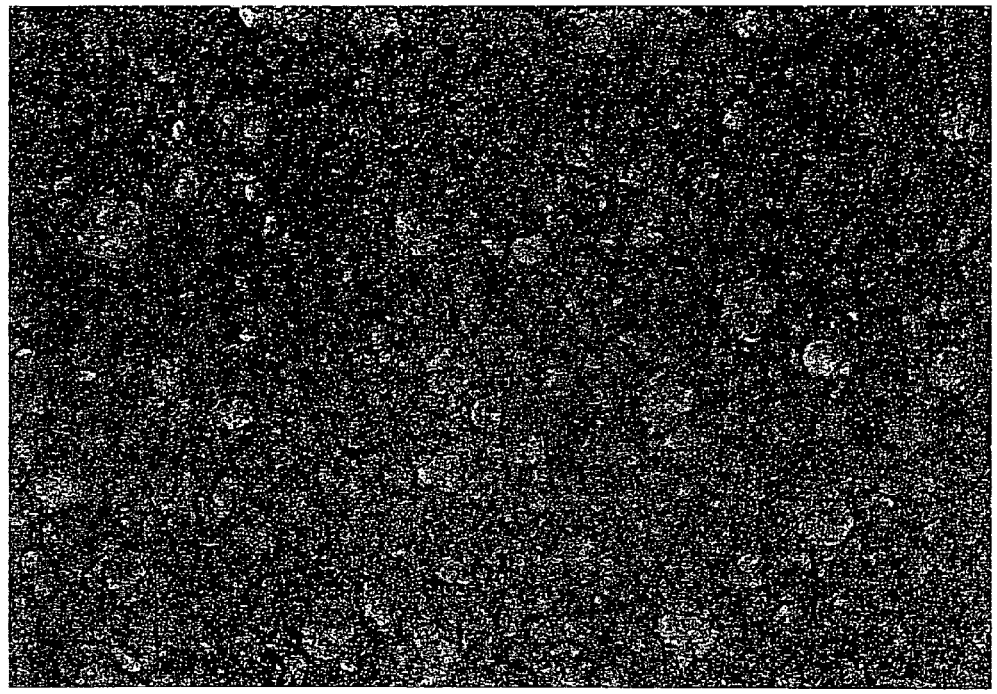
FIGS. 16A, 16B and 16C are scanning electron micrograph of a ruthenium film grown using CpRu(Et)(CO)$_2$, 300 cycles.
Figure 16B:
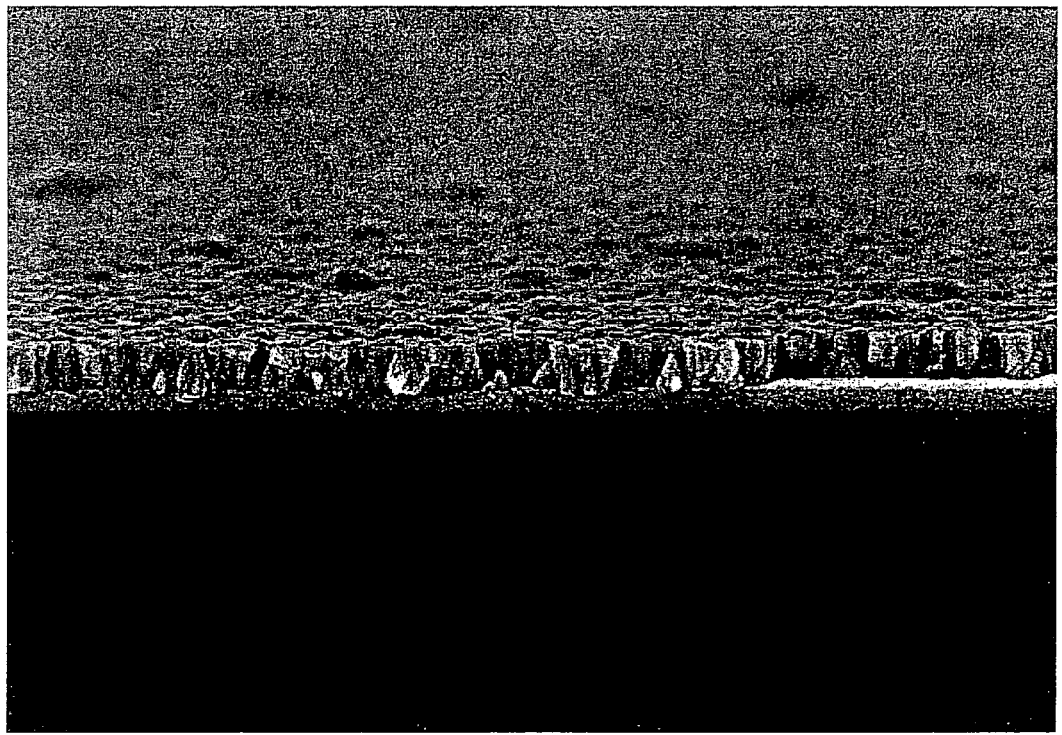
Figure 16C:
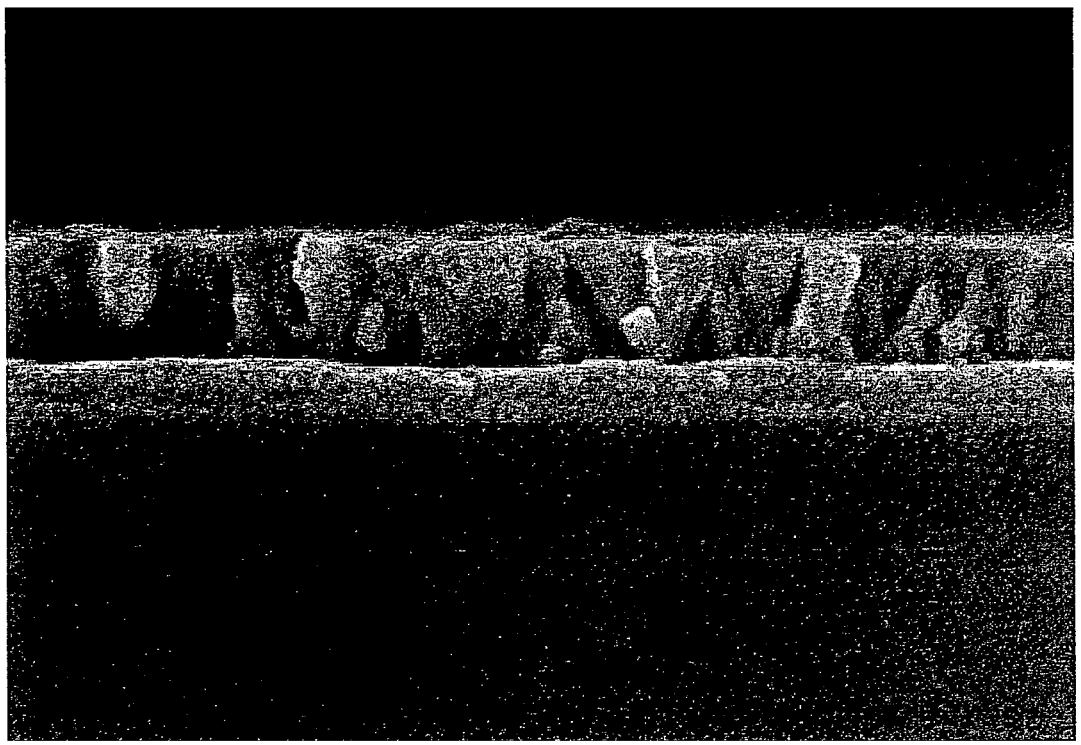

FIGS. 16A, 16B and 16C display three scanning electron micrographs of ruthenium films grown using $CpRuEt(CO)_2$. Continuous films with resistances less than 100 mega ohm/square were grown with RMS surface roughness of 2.1 nm.

The process of Example 6 was repeated using the various substrates and cycles listed in the table below. Good growth was seen on metal substrates throughout an 800 cycle run.

| | cycles | | | |
| --- | --- | --- | --- | --- |
| Substrate | 200 | 400 | 600 | 800 |
| Si (H-terminated) | No growth | Good growth, poor coverage | Growth, rough surface | Growth, very rough surface |
| SiO$_2$ (native oxide) | Some growth, poor coverage | Good growth good coverage | Growth, rough surface | Growth, very rough surface |
| Ta/Cu Metal | Good growth | Good growth | Good growth | Good growth |

Figure 17:
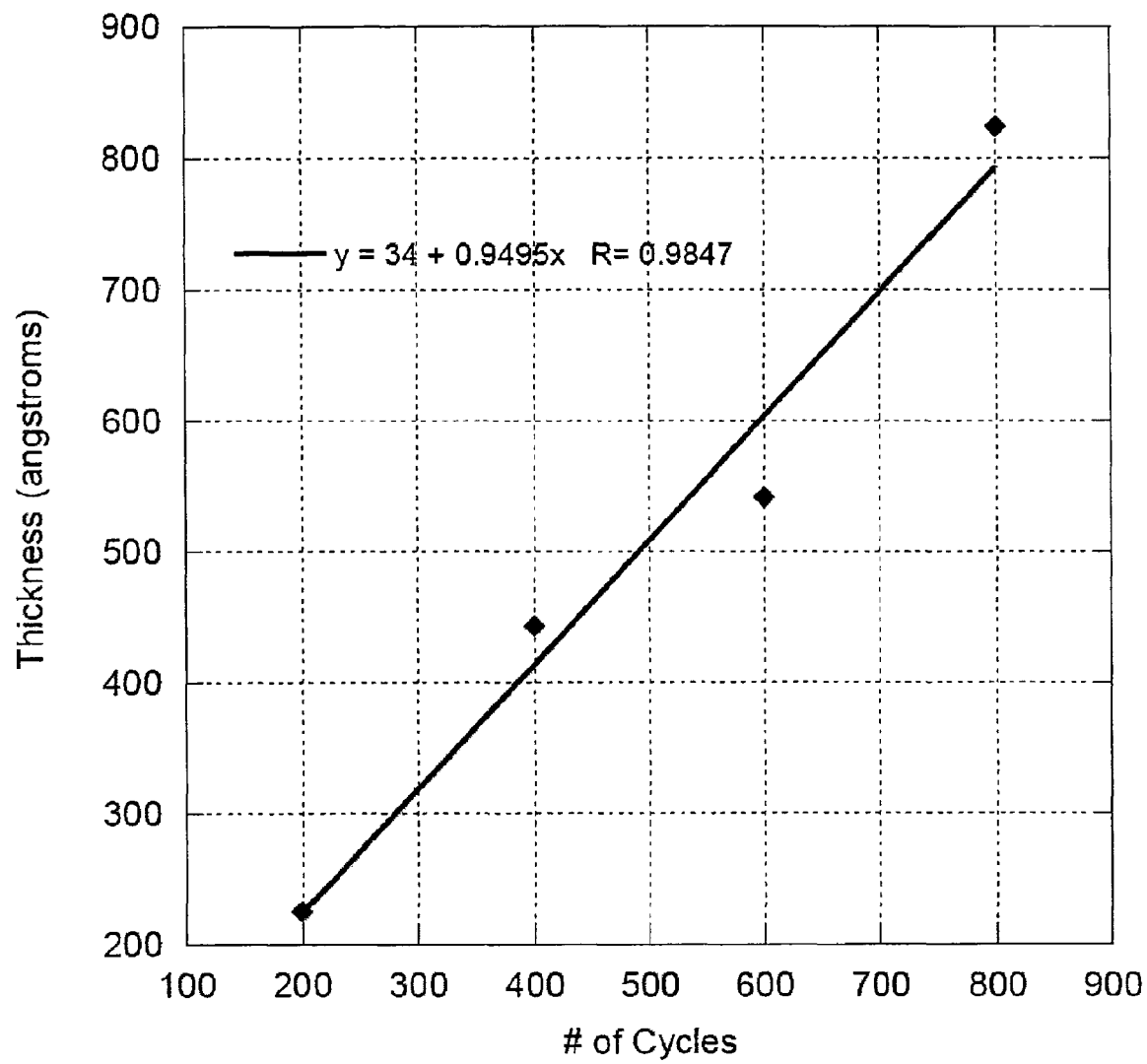
FIG. 17 is a graphical representation of ALD growth rate of CpRuEt(CO)$_2$ on Ta demonstrating thickness (angstroms) vs. # of cycles.
Figure 19:
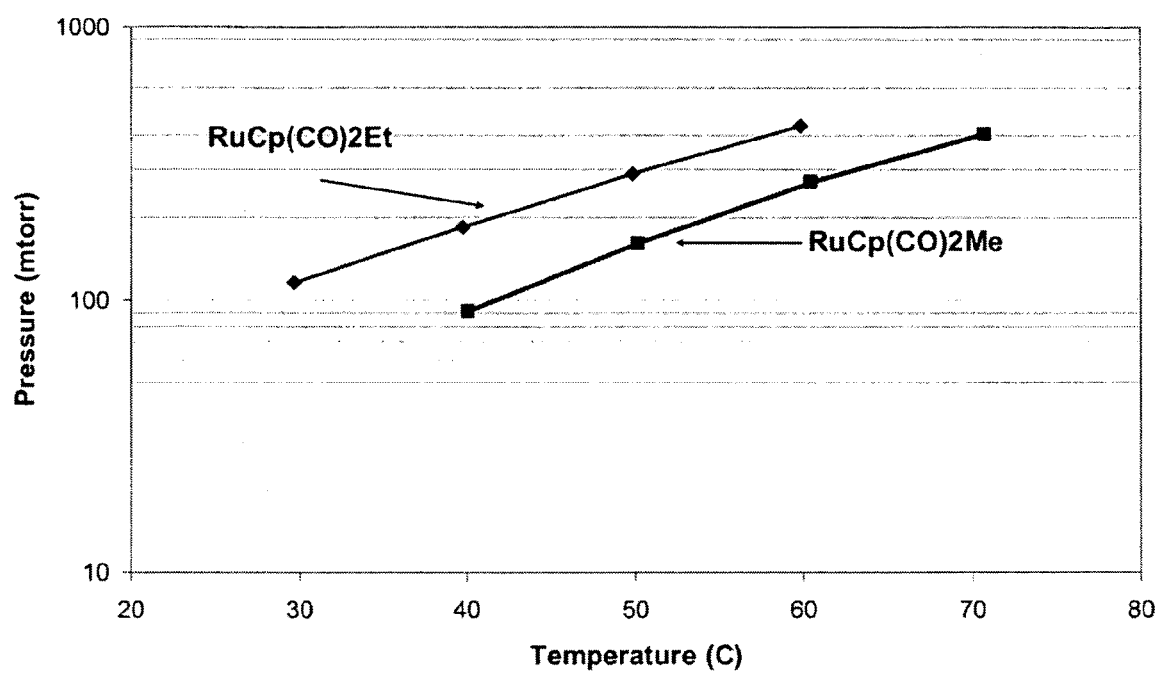
FIG. 19 is a graphical representation of vapor pressure data comparing pressure (mtorr) (y axis) vs. temperature (C) (x axis) of CpRu(Me)(CO)$_2$ and CpRu(Et)(CO)$_2$.

FIG. 17 is a graphical representation of ALD growth rate of ruthenium films on Ta substrate using $CpRuEt(CO)_2$. A growth rate of 0.95 Angstroms/cycle was achieved. Growth was measured by XRF and calibrated with a thick sample measured by SEM.

All patents and publications cited herein are incorporated by reference into this application in their entirety.

The words "comprise", "comprises", and "comprising" are to be interpreted inclusively rather than exclusively.

What is claimed is:

1. A method of forming a metal-containing thin film by atomic layer deposition, the method comprising delivering at least one precursor to a substrate, wherein the precursor corresponds in structure to Formula II:

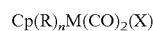

$Cp(R)_nM(CO)_2(X)$ (Formula II)

wherein:

M is Ru or Os;

R is $C_1$-$C_{10}$-alkyl;
X is $C_1$-$C_{10}$-alkyl;
n is zero, 1, 2, 3, 4 or 5.

2. The method of claim 1, wherein the at least one precursor corresponds in structure to Formula II wherein:
M is Ru;
R is methyl, ethyl, propyl or butyl;
X is methyl, ethyl, propyl or butyl; and
n is zero, 1 or 2.

3. The method of claim 1, wherein the at least one precursor corresponds in structure to Formula II wherein:
M is Ru;
R is methyl or ethyl;
X is methyl or ethyl; and
n is zero or 1.

4. The method of claim 1, wherein the at least one precursor corresponds in structure to Formula II wherein:
M is Os;
R is methyl, ethyl, propyl or butyl;
X is methyl, ethyl, propyl or butyl; and
n is zero, 1 or 2.

5. The method of claim 1, wherein the at least one precursor corresponds in structure to Formula II wherein:
M is Os;
R is methyl or ethyl;
X is methyl or ethyl; and
n is zero or 1.

6. The method of claim 1, wherein the at least one precursor corresponding in structure to Formula II is selected from the group consisting of:
(cyclopentadienyl)ruthenium(methyl)(dicarbonyl);
(cyclopentadienyl)ruthenium(ethyl)(dicarbonyl);
(cyclopentadienyl)osmium(methyl)(dicarbonyl);
(cyclopentadienyl)osmium(ethyl)(dicarbonyl);
(methylcyclopentadienyl)ruthenium(methyl)(dicarbonyl);
(ethylcyclopentadienyl)ruthenium(methyl)(dicarbonyl);
(propylcyclopentadienyl)ruthenium(methyl)(dicarbonyl);
(butylcyclopentadienyl)ruthenium(methyl)(dicarbonyl);
(methylcyclopentadienyl)ruthenium(ethyl)(dicarbonyl);
(ethylcyclopentadienyl)ruthenium(ethyl)(dicarbonyl);
(propylcyclopentadienyl)ruthenium(ethyl)(dicarbonyl);
(butylcyclopentadienyl)ruthenium(ethyl)(dicarbonyl);
(methylcyclopentadienyl)osmium(methyl)(dicarbonyl);
(ethylcyclopentadienyl)osmium(methyl)(dicarbonyl);
(propylcyclopentadienyl)osmium(methyl)(dicarbonyl);
(butylcyclopentadienyl)osmium(methyl)(dicarbonyl);
(methylcyclopentadienyl)osmium(ethyl)(dicarbonyl);
(ethylcyclopentadienyl)osmium(ethyl)(dicarbonyl);
(propylcyclopentadienyl)osmium(ethyl)(dicarbonyl); and
(butylcyclopentadienyl)osmium(ethyl)(dicarbonyl).

7. The method of claim 1, wherein the at least one precursor corresponding in structure to Formula II is selected from the group consisting of:
(cyclopentadienyl)ruthenium(methyl)(dicarbonyl);
(cyclopentadienyl)ruthenium(ethyl)(dicarbonyl);
(cyclopentadienyl)osmium(methyl)(dicarbonyl); and
(cyclopentadienyl)osmium(ethyl)(dicarbonyl).

8. The method of claim 1, wherein the at least one precursor corresponding in structure to Formula II is (cyclopentadienyl)ruthenium(ethyl)(dicarbonyl).

9. The method of claim 1, wherein the atomic layer deposition is photo-assisted atomic layer deposition.

10. The method of claim 1, wherein the atomic layer deposition is liquid injection atomic layer deposition.

11. The method of claim 1, further comprising delivering at least one appropriate co-reactant selected from the group consisting of hydrogen, hydrogen plasma, oxygen, air, water, ammonia, hydrazine, allylhydrazine, borane, silane, ozone and a combination thereof to the substrate.

12. The method of claim 1, wherein the at least one precursor is delivered to the substrate in pulses alternating with pulses of an oxygen source.

13. The method of claim 12, wherein the oxygen source is selected from $H_2O$, $O_2$ or ozone.

14. The method of claim 1, wherein the metal-containing thin film is used for memory and logic applications.

15. A method of forming a metal-containing thin film by chemical vapor deposition, the method comprising delivering at least one precursor to a substrate, wherein the precursor corresponds in structure to Formula II:

$$Cp(R)_nM(CO)_2(X) \quad \text{(Formula II)}$$

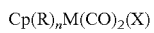

wherein:
M is Ru or Os;
R is $C_1$-$C_{10}$-alkyl;
X is $C_1$-$C_{10}$-alkyl; and
n is 0, 1, 2, 3, 4 or 5.

16. The method of claim 15, wherein the at least one precursor corresponds in structure to Formula II wherein:
M is Ru;
R is methyl, ethyl, propyl or butyl;
X is methyl, ethyl, propyl or butyl; and
n is zero, 1 or 2.

17. The method of claim 15, wherein the at least one precursor corresponds in structure to Formula II wherein:
M is Ru;
R is methyl or ethyl;
X is methyl or ethyl; and
n is zero or 1.

18. The method of claim 15, wherein the at least one precursor corresponds in structure to Formula II wherein:
M is Os;
R is methyl, ethyl, propyl or butyl;
X is methyl, ethyl, propyl or butyl; and
n is zero, 1 or 2.

19. The method of claim 15, wherein the at least one precursor corresponds in structure to Formula II wherein:
M is Os;
R is methyl or ethyl;
X is methyl or ethyl; and
n is zero or 1.

20. The method of claim 15, wherein the at least one precursor corresponding in structure to Formula II is selected from the group consisting of:
(cyclopentadienyl)ruthenium(methyl)(dicarbonyl);
(cyclopentadienyl)ruthenium(ethyl)(dicarbonyl);
(cyclopentadienyl)osmium(methyl)(dicarbonyl);
(cyclopentadienyl)osmium(ethyl)(dicarbonyl);
(methylcyclopentadienyl)ruthenium(methyl)(dicarbonyl);
(ethylcyclopentadienyl)ruthenium(methyl)(dicarbonyl);
(propylcyclopentadienyl)ruthenium(methyl)(dicarbonyl);
(butylcyclopentadienyl)ruthenium(methyl)(dicarbonyl);
(methylcyclopentadienyl)ruthenium(ethyl)(dicarbonyl);
(ethylcyclopentadienyl)ruthenium(ethyl)(dicarbonyl);
(propylcyclopentadienyl)ruthenium(ethyl)(dicarbonyl);
(butylcyclopentadienyl)ruthenium(ethyl)(dicarbonyl);
(methylcyclopentadienyl)osmium(methyl)(dicarbonyl);
(ethylcyclopentadienyl)osmium(methyl)(dicarbonyl);
(propylcyclopentadienyl)osmium(methyl)(dicarbonyl);
(butylcyclopentadienyl)osmium(methyl)(dicarbonyl);
(methylcyclopentadienyl)osmium(ethyl)(dicarbonyl);
(ethylcyclopentadienyl)osmium(ethyl)(dicarbonyl);
(propylcyclopentadienyl)osmium(ethyl)(dicarbonyl); and
(butylcyclopentadienyl)osmium(ethyl)(dicarbonyl).

21. The method of claim 15, wherein the at least one precursor corresponding in structure to Formula II is selected from the group consisting of:
(cyclopentadienyl)ruthenium(methyl)(dicarbonyl);
(cyclopentadienyl)ruthenium(ethyl)(dicarbonyl);
(cyclopentadienyl)osmium(methyl)(dicarbonyl); and
(cyclopentadienyl)osmium(ethyl)(dicarbonyl).

22. The method of claim 15, wherein the at least one precursor corresponding in structure to Formula II is (cyclopentadienyl)ruthenium(ethyl)(dicarbonyl).

23. The method of claim 15, wherein the chemical vapor deposition is photo-assisted chemical vapor deposition.

24. The method of claim 15, wherein the chemical vapor deposition is liquid injection chemical vapor deposition.

25. The method of claim 15, further comprising delivering at least one appropriate co-reactant selected from the group consisting of hydrogen, hydrogen plasma, oxygen, air, water, ammonia, hydrazine, allylhydrazine, borane, silane, ozone and a combination thereof to the substrate.

26. The method of claim 15, wherein the at least one precursor is delivered to the substrate in pulses alternating with pulses of an oxygen source.

27. The method of claim 26, wherein the oxygen source is selected from $H_2O$, $O_2$ or ozone.

28. The method of claim 15, wherein the metal-containing thin film is used for memory and logic applications.

29. A method of preparing a ruthenium precursor of Formula II, $$Cp(R)_n M(CO)_2(X) \qquad \text{(Formula II)}$$

wherein:
M is Ru;
R is $C_1$-$C_{10}$-alkyl;
X is $C_1$-$C_{10}$-alkyl; and
n is zero, 1, 2, 3, 4 or 5,
the method comprising:
reacting $Ru_3(CO)_{12}$ with $3(CpR_n)H$ to yield $3Ru(CpR_n)(CO)_2H$ and $6CO$;
reacting $Ru(CpR_n)(CO)_2H$ with BuLi to yield $Li[Ru(CpR_n)(CO)_2]$ and BuH; and
reacting $Li[Ru(CpR_n)(CO)_2]$ with XBr to yield $Ru(CpR_n)(CO)_2X$ and LiBr.

* * * * *

UNITED STATES PATENT AND TRADEMARK OFFICE
CERTIFICATE OF CORRECTION

PATENT NO.         : 8,481,121 B2                                    Page 1 of 1
APPLICATION NO.    : 12/670023
DATED              : July 9, 2013
INVENTOR(S)        : Ravi Kanjolia et al.

It is certified that error appears in the above-identified patent and that said Letters Patent is hereby corrected as shown below:

In the Specification

Column 7, line 7, replace "tent-butyl" with --*tert*-butyl--.

Column 7, line 57, replace "and/or IL" with --and/or II--.

Column 8, line 2, replace "*Chem. Yap.*" with --*Chem. Vap.*--.

Column 14, line 17, replace "with 30 scan of" with --with 30 sccm of--.

Column 15, line 36, replace "with 10 seem of" with --with 10 sccm of--.

Signed and Sealed this
Twenty-ninth Day of April, 2014

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,481,121 B2 | Page 1 of 1 |
| APPLICATION NO. | : 12/670023 | |
| DATED | : July 9, 2013 | |
| INVENTOR(S) | : Ravi Kanjolia et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 516 days.

Signed and Sealed this
Seventeenth Day of June, 2014

Michelle K. Lee
*Deputy Director of the United States Patent and Trademark Office*